(12) United States Patent
Haught et al.

(10) Patent No.: US 9,492,411 B2
(45) Date of Patent: Nov. 15, 2016

(54) MEDICATIONS FOR DEPOSITION ON BIOLOGICAL SURFACES

(71) Applicant: The Procter & Gamble Company, Cincinnati, OH (US)

(72) Inventors: John Christian Haught, West Chester, OH (US); Michael Reilly, Lebanon, OH (US); Steven Hamilton Hoke, West Chester, OH (US); Qingxin Lei, Liberty Township, OH (US); Yakang Lin, Liberty Township, OH (US); Koti Tatachar Sreekrishna, Mason, OH (US); Ashraf Traboulsi, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/693,915

(22) Filed: Apr. 23, 2015

(65) Prior Publication Data

US 2015/0306050 A1 Oct. 29, 2015

Related U.S. Application Data

(60) Provisional application No. 61/982,970, filed on Apr. 23, 2014, provisional application No. 61/982,968, filed on Apr. 23, 2014.

(51) Int. Cl.
*A61K 31/165* (2006.01)
*A61K 31/09* (2006.01)
(Continued)

(52) U.S. Cl.
CPC ............ *A61K 31/165* (2013.01); *A23G 4/06* (2013.01); *A61K 8/42* (2013.01); *A61K 8/46* (2013.01); *A61K 31/09* (2013.01); *A61K 31/137* (2013.01); *A61K 31/167* (2013.01); *A61K 31/192* (2013.01); *A61K 31/4402* (2013.01); *A61K 31/485* (2013.01); *A61Q 5/02* (2013.01);
(Continued)

(58) Field of Classification Search
CPC .................... A61K 31/485; A61K 31/165
USPC ........................ 514/289, 529, 617
See application file for complete search history.

(56) References Cited

U.S. PATENT DOCUMENTS 1,351,762 A 9/1920 King
3,111,127 A 11/1963 Jarboe
(Continued)

FOREIGN PATENT DOCUMENTS

EP 0310299 A1 4/1989
GB 1315626 A 5/1973
(Continued)

OTHER PUBLICATIONS

International Search Report and Written Opinion for 13818—PCT/US2015/027194 dated Jun. 29, 2015.
(Continued)

*Primary Examiner* — Kamal Saeed
*Assistant Examiner* — Janet L Coppins
(74) *Attorney, Agent, or Firm* — Alexandra S. Anoff

(57) ABSTRACT

Personal care compositions, such as oral medication compositions containing a flavor system comprising one or more coolants. The pleasant cool sensation provided by a coolant is enhanced in terms of quicker onset, greater intensity, impact or longer duration, which improves appeal and acceptability of the compositions to consumers.

12 Claims, 2 Drawing Sheets

(51) Int. Cl.
*A61K 31/137* (2006.01)
*A61K 31/167* (2006.01)
*A61K 31/192* (2006.01)
*A61K 31/4402* (2006.01)
*A61K 31/485* (2006.01)
*A23G 4/06* (2006.01)
*A61K 8/42* (2006.01)
*A61K 8/46* (2006.01)
*A61Q 5/02* (2006.01)
*A61Q 9/02* (2006.01)
*A61Q 11/00* (2006.01)
*C07C 233/73* (2006.01)
*C07C 233/75* (2006.01)
*C07C 237/10* (2006.01)
*C07C 255/44* (2006.01)
*C07C 323/33* (2006.01)

(52) U.S. Cl.
CPC .............. *A61Q9/02* (2013.01); *A61Q 11/00* (2013.01); *C07C 233/73* (2013.01); *C07C 233/75* (2013.01); *C07C 237/10* (2013.01); *C07C 255/44* (2013.01); *C07C 323/33* (2013.01); *A23V 2002/00* (2013.01)

(56) References Cited

U.S. PATENT DOCUMENTS

| | | |
|---|---|---|
| 3,917,613 A | 11/1975 | Humbert et al. |
| 3,991,178 A | 11/1976 | Humbert et al. |
| 4,029,759 A | 6/1977 | Humbert et al. |
| 4,136,163 A | 1/1979 | Watson et al. |
| 4,150,052 A | 4/1979 | Watson et al. |
| 4,153,679 A | 5/1979 | Rowsell et al. |
| 4,157,384 A | 6/1979 | Watson et al. |
| 4,178,459 A | 12/1979 | Watson et al. |
| 4,193,936 A | 3/1980 | Watson et al. |
| 4,226,988 A | 10/1980 | Watson et al. |
| 4,230,688 A | 10/1980 | Rowsell et al. |
| 4,459,425 A | 7/1984 | Amano et al. |
| 5,009,893 A | 4/1991 | Cherukuri et al. |
| 5,266,592 A | 11/1993 | Grub et al. |
| 5,451,404 A | 9/1995 | Furman |
| 5,608,119 A | 3/1997 | Amano et al. |
| 5,703,123 A | 12/1997 | Pelzer et al. |
| 5,725,865 A | 3/1998 | Mane et al. |
| 5,843,466 A | 12/1998 | Mane et al. |
| 5,968,025 A | 10/1999 | Roe et al. |
| 5,977,166 A | 11/1999 | Greenberg |
| 6,365,215 B1 | 4/2002 | Grainger et al. |
| 6,451,844 B1 | 9/2002 | Watkins et al. |
| 6,592,884 B2 | 7/2003 | Hofmann et al. |
| 6,884,903 B2 | 4/2005 | Lorenz et al. |
| 6,956,139 B2 | 10/2005 | Green et al. |
| 7,189,760 B2 | 3/2007 | Erman et al. |
| 7,741,355 B2 | 6/2010 | Moreno et al. |
| 7,772,266 B2 | 8/2010 | Moreno et al. |
| 7,893,072 B2 | 2/2011 | Reynolds et al. |
| 8,362,264 B2 | 1/2013 | Natarajan et al. |
| 8,389,730 B2 | 3/2013 | Natarajan et al. |
| 8,614,243 B2 | 12/2013 | Moreno et al. |
| 8,618,155 B2 | 12/2013 | Moreno et al. |
| 2005/0208113 A1 | 9/2005 | Roe et al. |
| 2006/0160713 A1 | 7/2006 | Sekine et al. |
| 2008/0118558 A1* | 5/2008 | Wei .................. A61K 9/0014 424/463 |

FOREIGN PATENT DOCUMENTS

| | | |
|---|---|---|
| WO | WO2005049553 A1 | 6/2005 |
| WO | WO2006103401 A2 | 10/2006 |
| WO | WO 2007/095340 A2 | 8/2007 |
| WO | WO2009067410 A1 | 5/2009 |
| WO | WO 2010/019730 A1 | 2/2010 |

OTHER PUBLICATIONS

Eccles, R., "Menthol and Related Cooling Compounds", J. Pharm. Pharmacol. 1994, 46: 618-630.

Emberger, R. and Hopp, R., "Synthesis and Sensory Characterization of Methol Enantiomers and Their Derivatives for the Use in Nature Identical Peppermint Oils", Specialty Chemicals, 1987, 7(3) 193-201.

McKemy, David D. "Therapeutic Potential of TRPM8 Modulators," The Open Drug Discovery Journal, 2010, 2, pp. 81-88.

Tolcher, Anthony W. et al. Preliminary Results from a Phase 1 Study of D-3263 HCl, a TRPM8 Calcium Channel Agonist, in Patients with Advanced Cancer Poster, EJC Suppl. vol. 8, No. 7, pp. 119, 2010.

* cited by examiner

MEDICATIONS FOR DEPOSITION ON BIOLOGICAL SURFACES

FIELD OF THE INVENTION

The present invention relates to personal care compositions, such as medications, containing a flavor system comprising one or more coolants, wherein the cool sensation provided by the coolant is enhanced in terms of quicker onset, greater intensity, and/or longer duration, thereby improving appeal and acceptability of the compositions to consumers.

BACKGROUND OF THE INVENTION

Medications, including liquid medicines and solid dosage forms, are routinely used by consumers to treat illness, mitigate symptoms, and/or to improve their health. However, many medications have a sensory experience that is not desirable to consumers. First, some medications taste overly bitter, which is caused by some actives and excipients in the formulations. Furthermore, there is often a lag between when a composition is orally ingested and when the consumer starts to feel relief. For instance, a consumer who has cold symptoms, including a sore throat and nasal congestion, may take multi-symptom relief (MSR) cold/flu medicine. However, she will not experience immediate relief from the cold symptoms, and instead she must wait for the product to be absorbed into the blood and become bio-available before her symptoms are alleviated.

The unpleasant taste and mouth sensations have been described as having a bitter, metallic, astringent, salty, numbing, stinging, burning, or prickling, and even irritating aspects. To mitigate the negative aesthetics in medications, medications often contain flavors, sweeteners, and sensates, to help improve the consumer's experience. In addition, sensate molecules in medications can convey a signal of efficacy and provide some relief from symptoms before the actives become bio-available. Such signals of efficacy include cooling, tingling, numbing, warming, sweetness, and rheological sensations such as phase change and fizzing or bubbling.

A large number of coolant compounds of natural or synthetic origin have been described. The most well-known compound is menthol, particularly 1-menthol, which is found naturally in peppermint oil, notably of *Mentha arvensis* L and *Mentha viridis* L. Of the menthol isomers, the 1-isomer occurs most widely in nature and is typically what is referred by the name menthol having coolant properties. L-menthol has the characteristic peppermint odor, has a clean fresh taste and exerts a cooling sensation when applied to the skin and mucosal surfaces. Other isomers of menthol (neomenthol, isomenthol and neoisomenthol) have somewhat similar, but not identical odor and taste, i.e., some having disagreeable notes described as earthy, camphor, musty. The principal difference among the isomers is in their cooling potency. L-menthol provides the most potent cooling, i.e., having the lowest cooling threshold of about 800 ppb, i.e., the concentration where the cooling effect could be clearly recognized. At this level, there is no cooling effect for the other isomers. For example, d-neomenthol is reported to have a cooling threshold of about 25,000 ppb and 1-neomenthol about 3,000 ppb. (R. Emberger and R. Hopp, "Synthesis and Sensory Characterization of Menthol Enantiomers and Their Derivatives for the Use in Nature Identical Peppermint Oils," Specialty Chemicals (1987), 7(3), 193-201). This study demonstrated the outstanding sensory properties of 1-menthol in terms or cooling and freshness and the influence of stereochemistry on the activity of these molecules.

Among synthetic coolants, many are derivatives of or are structurally related to menthol, i.e., containing the cyclohexane moiety, and derivatized with functional groups including carboxamide, ketal, ester, ether and alcohol. Examples include the ρ-menthanecarboxamide compounds, such as N-ethyl-ρ-menthan-3-carboxamide, known commercially as "WS-3", and others in the series, such as WS-5 (N-ethoxycarbonylmethyl-ρ-menthan-3-carboxamide), WS-12 [N-(4-methoxyphenyl)-ρ-menthan-3-carboxamide], and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D); menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Mane. TK-10 is described in U.S. Pat. No. 4,459,425 to Amano et al. Other alcohol and ether derivatives of menthol are described e.g., in GB 1,315,626 and in U.S. Pat. Nos. 4,029,759; 5,608,119; and 6,956,139. WS-3 and other carboxamide cooling agents are described for example in U.S. Pat. Nos. 4,136,163; 4,150,052; 4,153,679; 4,157,384; 4,178,459 and 4,230,688. Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)-ρ-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. Other N-substituted ρ-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310 299 and in U.S. Pat. Nos. 3,111,127; 3,917,613; 3,991,178; 5,5703,123; 5,725,865; 5,843,466; 6,365,215; 6,451,844; and 6,884,903. Ketal derivatives are described, e.g., in U.S. Pat. Nos. 5,266,592; 5,977,166 and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112. Reviews on the coolant activity of menthol and synthetic coolants include H. R. Watson, et al. J. Soc. Cosmet. Chem. (1978), 29, 185-200 and R. Eccles, J. Pharm. Pharmacol., (1994), 46, 618-630.

The present invention provides medication compositions comprising one or more coolants that can be used in medications, wherein the cooling and refreshing sensation provided by the coolant(s) is potentiated in terms of onset, intensity, and/or duration.

SUMMARY OF THE INVENTION

A medication composition providing a cool sensation wherein the composition comprises a compound comprising the following structure:

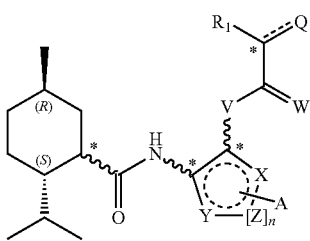

$R_1$ is selected from H, alkyl, amino alkyl, alkoxy;
$Q=H_2$, O, $-OR_1$, $-N(R_1)_2$, $-OPO(OR_1)_x$, $-PO(OR_1)_x$, $-P(OR_1)_x$ (where x=1-2;
$V=NR_1$, O, $-OPO(OR_1)_x$, $-PO(OR_1)_x$, $-P(OR_1)_x$ where x=1-2;
$W=H_2$, O;
X, Y=independently selected from H, aryl, naphthyl for n=0;
X, Y=aliphatic $CH_2$ or aromatic CH for n≥1 and Z is selected from aliphatic $CH_2$, aromatic CH, or heteroatom;
A=lower alkoxy, lower alkylthio, aryl, substituted aryl or fused aryl; and
stereochemistry is variable at the positions marked*.

These and other features, aspects, and advantages of the present invention will become evident to those skilled in the art from the detailed description that follows.

DETAILED DESCRIPTION OF THE INVENTION

Figure 1:
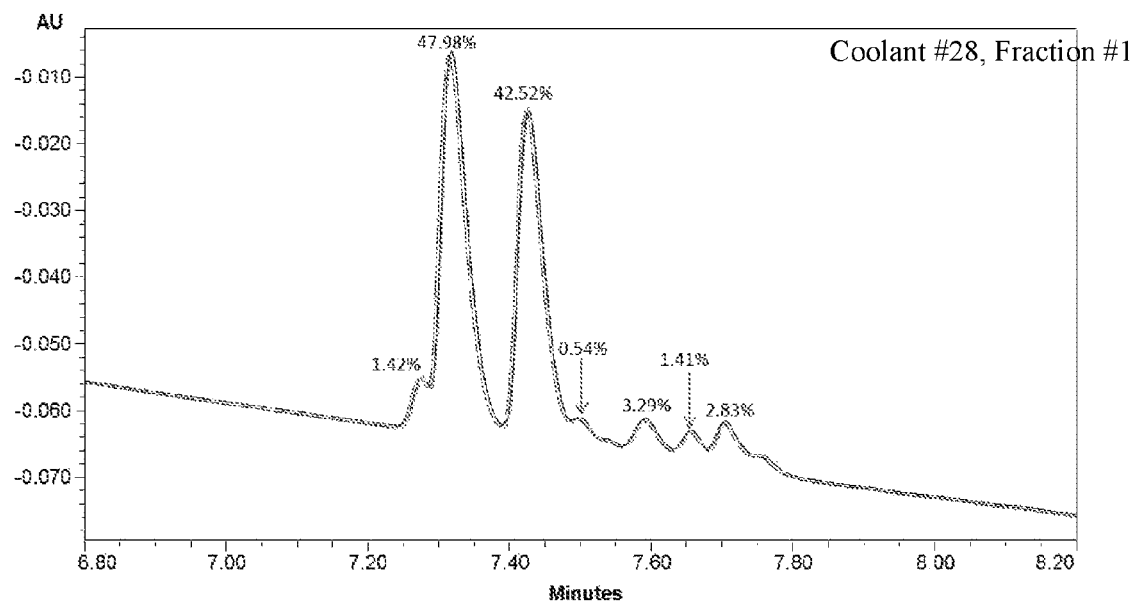
FIG. 1 UV chromatogram overlays of three replicate injections of compound 28, fraction 1. The percentages of relative peak area are shown above each isomeric compound observed within this mixture. All peaks appear at nominal m/z 374 in the QDa mass spectra, indicating that these are isomeric species.

The present invention is directed to the discovery that certain cyclohexanecarboxamide structures deliver the means to drive a cooling response at low concentrations. It has been discovered that cyclohexanecarboxamide, 5-methyl-2-(1-methylethyl)-N-(2-phenyl)-, (1R,2S,5R) (CAS#824947-52-6) and cyclohexanecarboxamide, 5-methyl-2-(1-methylethyl)-N-(2-phenylethyl)-, (1R,2S,5R) (CAS#847564-71-0) structures with 2-amino-propanamide (CAS#4726-84-5) have enhanced long lasting cooling properties and cyclohexanecarboxamide, 5-methyl-2-(1-methylethyl)-N-phenyl-, (1R,2S,5R) and cyclohexanecarboxamide, 5-methyl-2-(1-methylethyl)-N-1-naphthalenyl-(1R,2S, 5R) (CAS#863091-95-6) structures with an aminoethane (CAS#75-04-7) moiety deliver a warming sensation. Both types of cyclohexanecarboxamide (cooling and warming) are efficacious at low use levels (1-10 ppm). The stereochemistry assigned to the compounds above is based on the dominant isomer (1R,2S,5R) derived from the menthol starting material. One or more additional isomers and/or enantiomers may occur due to the additional chiral sites built out from the amide linkage.

Structures built off of the cyclohexanecarboxamide backbone have been applied as anti-cancer agents as disclosed in WO 2009/067410. As shown in U.S. Pat. No. 4,150,052, only a select few of the cyclohexanecarboxamide derivatives had noticeable cooling. The molecules disclosed in WO 2009/067410 were evaluated for their TRPM8 activity in relation to the destruction prostate cancer cells. The data shown herein illustrates that activating TRPM8 does not necessarily mean that a cooling sensation will be observed. Thus cooling would have been an undesirable effect and something they would have avoided.

The present invention is thus based on the discovery that select molecules can be used to drive a cooling response when formulated into consumer products. A second object of this invention shows the discovery that select cyclohexanecarboxamide derivatives can provide long lasting cooling at very low levels, allowing for formulation efficiencies, in particular coolant compounds (coolants), such as described below.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

As used herein, "dose" refers to a volume of medication, such as liquid medication or oral dosage unit, containing an amount of a drug active suitable for administration on a single occasion, according to sound medical practice. A dose can be orally administered. In one example, a dose can be a liquid medication and can be about 30 mL, in another example about 25 mL, in another example about 20 mL, in another example about 15 mL, and in another example about 10 mL. In another example, a dose of liquid medication can be from about 10 mL to about 75 mL, in another example from about 15 mL to about 50 mL, in another example from about 25 mL to about 40 mL, and in another example from about 28 mL to about 35 mL. In another example, the dose can be a solid dosage form and can be from about 5 g to about 25 mg, in another example from about 3 g to about 100 mg, in another example from about 2 g to about 250 mg, in another example from about 1.6 g to about 500 mg, and in another example from about 1 g to about 750 mg. In one example, the dose can be a solid dosage form wherein one dose is about 3 g and in another example one dose is about 1.6 g. The concentration of active ingredients can be adjusted to provide the proper doses of actives given the liquid dose size. In one example, the dose is intended to be administered every 4 hours, in another example every 6 hours, in another example every 8 hours, and in another example every 12 hours.

As used herein, "medication" refers to medications, such as pharmaceuticals, including prescription medications, over-the-counter medications, behind-the-counter medications and combinations thereof. In some examples, a medication can be a supplement which can contain vitamins, minerals, and botanicals (VMS).

Medication compositions can be in any suitable form including liquid compositions and solid oral dosage forms. Non limiting examples of liquid compositions can include syrups including cough syrups, respiratory preparations including MSR cold/flu medication, beverages, supplemental water, foam compositions, gel compositions, particles suspended in a liquid formulation, a solid in a gelatin or foam, saline wash and combinations thereof. Non-limiting examples of solid oral dosage forms can include tablets, capsules, caplets, sachets, sublingual dosage forms, buccal dosage forms, soft gels including Vicks® LiquiCaps™ and other liquid filled capsules, dissolvable dosage forms including dissolvable strips, films, gums including a center filled gum, gummies including a center filled gummy, lozenges, center filled tablets, powder, granules, pellets, microspheres, nanospheres, beads, or nonpareils, and combinations thereof. Tablets can include compressed tablets, chewable tablets, dissolvable tablets, and the like. Tablets can include compressed tablets, chewable tablets, dissolvable tablets, and the like. In some examples, the medication can be applied to the skin, in an ointment such as Vicks® VapoRub®. In other examples, the medication can be inhaled, such as a nose spray or inhaler. In other examples, the medication can be in a drink, such as a warm beverage. In other examples, the medication can contain a pharmaceutical active. In other examples, the medication does not contain a pharmaceutical active and/or VMS but can alleviate symptoms and/or provide a health benefit at least in part, through the cooling sensation.

The medications can be in a form that is directly deliverable to the mouth, throat, and/or skin. In some example, the medication compositions can be delivered by a delivery device selected from droppers, pump, sprayers, liquid dropper, saline wash delivered via nasal passageway, cup, bottle, canister, pressurized sprayers, atomizers, air inhalation devices, squeezable sachets, power shots, blister cards, and other packaging and equipment, and combinations thereof. The sprayer, atomizer, and air inhalation devices can be associated with a battery or electric power source. By "personal care composition" is meant a product, which in the ordinary course of usage is applied to or contacted with a body surface to provide a beneficial effect. Body surface includes skin, for example dermal or mucosal; body surface also includes structures associated with the body surface for example hair, teeth, or nails. Examples of personal care compositions include a product applied to a human body for improving appearance, cleansing, odor control, general aesthetics, or for health and wellness. Non-limiting examples of personal care compositions include medicines including solid dosage forms and liquid compositions; oral care compositions, such as, dentifrice, mouth rinse, mousse, foam, mouth spray, lozenge, chewable tablet, chewing gum, tooth whitening strips, floss and floss coatings, breath freshening dissolvable strips, denture care product, denture adhesive product; after shave gels and creams, pre-shave preparations, shaving gels, creams, or foams, moisturizers and lotions; cough and cold compositions, gels, gel caps, and throat sprays; leave-on skin lotions and creams, shampoos, body washes, ointments applied to the throat, chest and other parts of the body, such as Vicks® Vaporub®; hair conditioners, hair dyeing and bleaching compositions, mousses, shower gels, bar soaps, toile bars, antiperspirants, deodorants, depilatories, lipsticks, foundations, mascara, sunless tanners and sunscreen lotions; feminine care compositions, such as lotions and lotion compositions directed towards absorbent articles; baby care compositions directed towards absorbent or disposable articles; and oral cleaning compositions for animals, such as dogs and cats.

In one example, the present invention can be directed towards a liquid medication, in particular a liquid medication intended to be used by someone who has cold/flu or allergy symptoms such as congestion, sore throat, itchy throat, itchy nose, cough, and combinations thereof. The liquid medication can provide on demand relief to reduce pain and itching in the nasal cavity and throat, reduce coughing, and/or reduce congestion. The preparation can work to physically coat the mouth and throat creating a soothing barrier over the epithelial cells that line the throat layer. In addition, the composition can create a plume that can further help reduce congestion. The preparation can additionally, reduce inflammation, which can help relieve pain associated with a cough and/or sore throat. In one example, the liquid medication does not contain actives. In another example, the liquid medication does contain actives, which can include a pain reliever, a decongestant, and/or a cough suppressant. In one example, the liquid medication can be swallowed. In another example, the liquid medication can be swished and/or gargled and then expectorated.

The term "dispenser", as used herein, means any pump, tube, or container suitable for dispensing compositions such as medications. The medications can be in ointments, gels, foams, liquids, etc.

The components of the present compositions are described in the following paragraphs.

| SEQ ID NO | Sequence |
|---|---|
| 1 | Human TRPV1 DNA sequence |
| 2 | Human TRPA1 DNA sequence |
| 3 | Human TRPM8 DNA sequence |

The term "TRPV1" or "TRPV1 receptor", as used herein, refers to the transient receptor potential vanilloid receptor 1, which is a ligand-gated, non-selective cation channel preferentially expressed on small-diameter sensory neurons and detects noxious as well as other substances. The TRPV1 receptor is provided as SEQ ID NO: 1. The TRPV1 receptor responds to, for example, both noxious and painful stimuli. A noxious stimulus would include those that give a burning (i.e. hot) sensation.

The term "TRPV1 agonist", as used herein, refers to any compound, which at a concentration of 1 mM gives a calcium flux count of at least 1000 counts or 20% above the background level of calcium present in the cell according to the FLIPR method, as discussed herein. The term "count" is defined as the change in fluorescence of the cell lines due to the influx of calcium across the cell membrane, which reacts with the calcium sensitive dye present within the cells.

The term "TRPV1 antagonist", as used herein, refers to any compound which at a concentration of 1 mM gives a reduction in calcium flux count of at least 1000 counts or 20% below the activation of TRPV1 receptor by 350 μM capsaicin.

The term "TRPV1 desensitizer", as used herein, refers to any compound, which shows agonist activity and causes a decrease in activation by a known TRPV1 agonist.

The term "TRPA1" or "TRPA1 receptor", as used herein, refers to the transient receptor potential cation channel, subfamily A, member 1, having a large cysteine-rich N-terminus that contains 18 predicted ankyrin repeats. The TRPA1 receptor is provided as SEQ ID NO: 2. TRPA1 is a ligand-gated, non-selective cation channel preferentially expressed on small diameter sensory neurons.

The term "TRPA1 agonist", as used herein, refers to any compound, which at a concentration of 1 mM gives a calcium flux count of at least 1000 counts or 20% above the background level of calcium present in the cell according to the FLIPR method, as discussed herein. The term "count" is defined as the change in fluorescence of the cell lines due to the influx of calcium across the cell membrane, which reacts with the calcium sensitive dye present within the cells.

The term "TRPA1 antagonist", as used herein, refers to any compound, which at a concentration of 1 mM gives a reduction in calcium flux count of at least 1000 counts or 20% below the activation of TRPA1 receptor by 50 mM allyl isothiocyanate.

The term "TRPA1 desensitizer", as used herein, refers to any compound, which shows agonist activity and causes a decrease in activation by a known TRPA1 agonist.

The term "TRPM8" or "TRPM8 receptor", as used herein, refers to cold- and menthol-sensitive receptor (CMR1) or TRPM8. The TRPM8 nomenclature for the receptor comes from its characterization as a non-selective cation channel of the transient receptor potential (TRP) family that is activated by stimuli including low temperatures, menthol and other chemical coolants. The TRPM8 receptor is provided as SEQ ID NO: 3.

The cooling receptor conventionally known as TRPM8 or the menthol receptor has been demonstrated as a means to differentiate intensity and duration of organic molecules that initiate and propagate the non-thermal cooling perception (D. D. Mckemy, *The Open Drug Discovery Journal* 2:81-88 2010). McKemy reported the EC50 values of many agonists to TRPM8 which span the range of 100 nM to 19 mM, thus showing the channel can be activated across a wide range of structures at varying concentrations. This channel also has the nomenclature of CRM1 and TRPP8. The later was designated as such due to its identification with prostate cells, where it was employed as a means to identify molecules targeted towards prostate cancer.

The term "TRPM8 agonist", as used herein, refers to any compound, which when added to a TRPM8 receptor, according to the FLIPR method, as discussed herein, produces any increase in fluorescence over background.

The term "TRPM8 antagonist", as used herein, refers to any compound, which does not show any agonistic activity when directly added and inhibits activation of the TRPM8 receptor by a known TRPM8 agonist. Using the FLIPR method, as discussed herein a molecule that has >20% reduction in calcium flux compared to the WS5 activated TRPM8 receptor is considered a TRPM8 antagonist.

The term potency, as defined by the Merck Manual, refers to the concentration (EC50) or dose (ED50) of a chemistry required to produce 50% of the chemistry's maximal effect as depicted by a graded dose-response curve. EC50 equals Kd (Dissociation constant, which is a measure of 50% of the substance in question bound to the receptor) when there is a linear relationship between occupancy and response. Often, signal amplification occurs between receptor occupancy and response, which results in the EC50 for response being much less (ie, positioned to the left on the abscissa of the log dose-response curve) than KD for receptor occupancy. Potency depends on both the affinity of chemistry for its receptor, and the efficiency with which chemistry-receptor interaction is coupled to response. The dose of chemistry required to produce an effect is inversely related to potency. In general, low potency is important only if it results in a need to administer the chemistry in large doses that are impractical. Quantal dose-response curves provide information on the potency of chemistry that is different from the information derived from graded dose-response curves. In a quantal dose-response relationship, the ED50 is the dose at which 50% of individuals exhibit the specified quantal effect.

Coolants or compounds that have a physiological cooling effect particularly on oral and other mucosal surfaces and skin are common ingredients in a wide variety of products, including edible compositions, personal care compositions, and in flavor or perfume compositions. Examples of edible compositions include confectionery, candies, chocolate, chewing gum, beverages and oral medicines. Personal care compositions, including oral care compositions, have been described previously. The pleasant cooling sensation provided by coolants contributes to the appeal and acceptability of the products. In particular, medications, can be formulated with coolants because they provide a desirable sensory experience. In particular, consumers with a cold/flu may enjoy a cool feeling in their mouth and throat to help relieve their sore throats and can also provide overall cooling to their oral cavity, which may feel dry and warm due to a fever and/or allergies. Furthermore, the cool feeling may also feel pleasing when applied to skin, such as when using an ointment, especially if the user is warm with a fever.

It is now well established that sensations such as cool or cold can be attributed to activation of receptors at peripheral nerve fibers by a stimulus such as low temperature or a chemical coolant, which produces electrochemical signals that travel to the brain, which then interprets, organizes and integrates the incoming signals into a perception or sensation. Different classes of receptors have been implicated in sensing cold temperatures or chemical coolant stimuli at mammalian sensory nerve fibers. Among these receptors, a major candidate involved in sensing cold has been identified and designated as cold- and menthol-sensitive receptor (CMR1) or TRPM8. The TRPM8 nomenclature for the receptor comes from its characterization as a non-selective cation channel of the transient receptor potential (TRP) family, which is activated by stimuli including low temperatures, menthol and other chemical coolants. However, the precise mechanisms underlying the perception of a pleasant cooling sensation on skin or oral surfaces are presently not clearly understood. While it has been demonstrated that the TRPM8 receptor is activated by menthol and other coolants, it is not fully understood what other receptors may be involved, and to what extent these receptors need to be stimulated or perhaps suppressed in order for the overall perceived sensation to be pleasant, cooling and refreshing. For example, menthol is widely used as a cooling agent, but menthol can also produce other sensations including tingling, burning, prickling and stinging as well as a minty smell and bitter taste. Thus, it can be inferred that menthol acts on many different receptors, including cold, warm, pain and taste receptors.

Examples of solvents that can be used to solubilize compounds of the present invention, such as compound 28—as discussed below, are based upon solubility parameters and cohesion properties explained by Charles Hansen in "Hansen Solubility Parameters: A User's Handbook" by Charles M. Hansen, CRC Press (2007) and in "The CRC Handbook and Solubility Parameters and Cohesion Parameters," Edited by Allan F. M. Barton (1999). Each material is defined by three points in 3D space and these three points are known as the Hansen Solubility Parameters (HSP) which may be defined as follows.

Solubility parameters are theoretically calculated numerical constants, which are a useful tool in predicting the ability of a solvent material to dissolve a particular solute. When the solubility parameters of a solvent falls within the solubility parameter range of a solute, i.e., the material to be dissolved, solubilization of the solute is likely to occur. There are three Hansen empirically and theoretically derived solubility parameters, a dispersion-force component ($\delta_D$), a polar or dipole interaction component ($\delta_P$) and a hydrogen-bonding component ($\delta_H$). Each of the three parameters (i.e., dispersion, polar and hydrogen bonding) represents a different characteristic of solvency, or solvent capability. In combination, the three parameters are a measure of the overall strength and selectivity of a solvent. The Total Hansen solubility parameter, which is the square root of the sum of the squares of the three parameters mentioned previously, provides a more general description of the solvency of the solvents. Individual and total Solubility Parameter units are given in $MPa^{0.5}$. Solubility parameters for a material may then be plotted in a normal three-dimensional graph. From the location ($\delta_D$, $\delta_P$, $\delta_H$), a radius is projected to form a sphere, which encompasses a region of solubility such that any solvent whose parameters reside within this space should dissolve the solute in question. The distance between the HSP coordinate of material (i.e., the solute) to the HSP coordinates of material (solvent) is designated herein as Ra. The 3D distance, Ra, is defined by the equation: $Ra^2=4(\delta_{D1}-\delta_{D2})^2+(\delta_{P1}-\delta_{P2})^2+(\delta_{H1}-\delta_{H2})^2$ The sphere equation of Hansen was calculated to center the target molecules of choice, in this case, compound 28 and the various isomers (L, D, and neo) and enantiomers of each. The target Polar, Dispersive, and Hydrogen Bonding HSP are the Hansen solubility parameters of the target molecule as calculated by "Molecular Modeling Pro" software, version 5.1.9 (ChemSW, Fairfield Calif., www.chemsw.com) or Hansen Solubility from Dynacomp Software. The solubility parameters of every solvent in this analysis were also calculated via this software. Within the sphere having a radius $R_a=14$ are solvents into which compound 28 and isomer materials will be soluble. For solubility >5% in the selected solvents, the preferred range of $\delta_{dispersion}$ is ±3 units, from about 15.2 to 21.2 $(MPa)^{0.5}$. The preferred range of $\delta_{polarity}$ is ±6 units, from about 0 to 10.8 $(MPa)^{0.5}$. The preferred range of $\delta_{Hydrogen\ bonding}$ is ±13 units, from about 0 to 25 $(MPa)^{0.5}$. The HSP of compound 28 were calculated as dispersion=17.8, polarity=5.6, and hydrogen bonding=9.0. Non-limiting examples of flavor and fragrance raw materials having suitable Hansen Solubility Parameters used to solubilize the carboxamide derivative include menthone, carvone, pine oil, cinnamic aldehyde, ethanol, benzyl alcohol, eucalyptol, 1,2-propane diol, 1,3-propane diol, hexane, ethanolamine, cyclodextrins, and triacetin.

Ideally, a coolant can produce a cooling or freshness sensation similar to that produced by menthol, but without certain of the disadvantages associated with menthol, such as flavor modification, bitter aftertaste, off-flavor, strong odor and burning or irritating sensation, particularly at high concentrations. It is desirable that the coolant compounds barely possess a distinctive odor or flavor while providing a pleasant fresh cool sensation of prolonged duration, in order that the effect can still be perceived for a considerable time after use, for example, longer than 15 minutes. Menthol generally provides an initial high cooling impact, but its effect is somewhat transient in that the cool sensation drops sharply within a few minutes after use. By contrast, a number of longer lasting coolant compounds may fail to provide an immediate cooling perception, i.e., within a few seconds of application, particularly when used at low levels. Thus there is a continuing need for means to potentiate the activity of coolant chemicals, in terms of quickening the onset of the cooling sensation, intensifying the cooling sensation, especially at lower concentrations, and producing a longer lasting sensation of cooling and freshness than what menthol provides.

As stated previously, the present invention is directed to the discovery that specific 5-methyl-2-(1-methylethyl)-N-(2-phenyl)-, (1R,2S,5R) cyclohexanecarboxamide structures, as shown below, deliver the means to drive a cooling response at low concentrations.

Structure I, which includes compounds of the present invention, as shown below, and which includes compound 28, represents a genus that has been surprisingly found to be useful as modulators of TRPM8 activation. Structure I represents a heteroalkyl substituted aryl or heteroalkyl-aryl substituted alkyl carboxamide of methanol having the shown below structure and including any acceptable salts or solvates thereof; wherein:

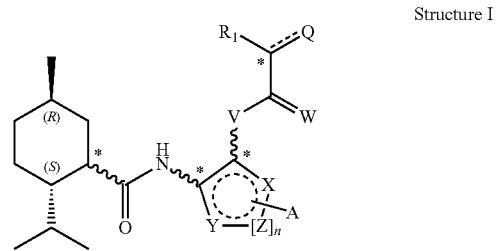

Structure I $R_1$ is selected from H, alkyl, amino alkyl, alkoxy;
$Q=H_2$, O, $—OR_1$, $—N(R_1)_2$, $—OPO(OR_1)_x$, $—PO(OR_1)_x$, $—P(OR_1)_x$ (where x=1-2;
$V=NR_1$, O, $—OPO(OR_1)_x$, $—PO(OR_1)_x$, $—P(OR_1)_x$ where x=1-2;
$W=H_2$, O;
X, Y=independently selected from H, aryl, naphthyl for n=0;
X, Y=aliphatic $CH_2$ or aromatic CH for n≥1 and Z is selected from aliphatic $CH_2$, aromatic CH, or heteroatom;
A=lower alkoxy, lower alkylthio, aryl, substituted aryl or fused aryl; and
stereochemistry is variable at the positions marked*.

A number of stereoisomers are contemplated in the above Structure I, where substitution is allowed and the relative configuration of each stereo center will dictate the activity towards the receptor.

While it is known that the stereochemistry of side chain groups may be important to the activity of the molecule, the activity of these compounds in vivo is highly unpredictable. In some cases, isomers of the same molecule may have comparable activity. In other cases, stereoisomers of the same molecule could have enhanced or diminished activity towards the receptor. In some cases, individual stereoisomers may have no activity.

Specific compounds of interest may derive from the 1R, 2S, 5R configuration found in natural (−)-menthol. In these cases, the stereoisomeric derivatives of 1R, 2S, 5R-menthyl carboxamide will be found in the substituted alkyl side chain fragment of the molecule. While the 1R, 2S, 5R configuration is known to be important to activity, the 1S,2S,5R neo-isomer of N-substituted menthyl carboxamide derivatives has also shown promise.

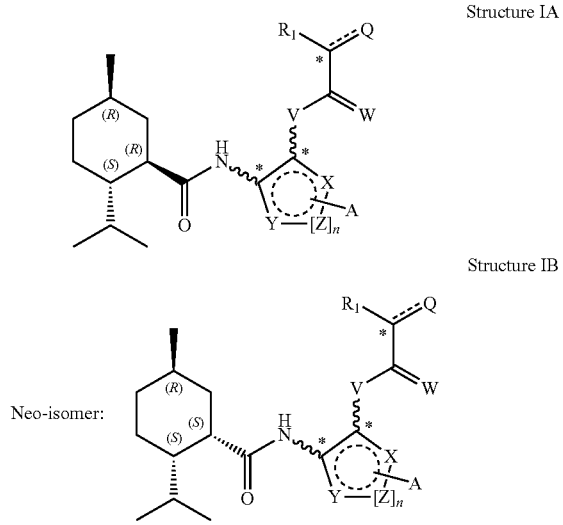

$R_1$ is selected from H, alkyl, amino alkyl, alkoxy;
Q=$H_2$, O, —$OR_1$, —$N(R_1)_2$, —$OPO(OR_1)_x$, —$PO(OR_1)_x$, —$P(OR_1)_x$ where x=1-2;
V=$NR_1$, O, —$OPO(OR_1)_x$, —$PO(OR_1)_x$, —$P(OR_1)_x$ where x=1-2;
W=$H_2$, O;
X, Y=independently selected from H, aryl, naphthyl for n=0;
X, Y=aliphatic $CH_2$ or aromatic CH for n≥1 and Z is selected from aliphatic $CH_2$, aromatic CH, or heteroatom;
A=lower alkoxy, lower alkylthio, aryl, substituted aryl or fused aryl; and
stereochemistry is variable at the positions marked*.

In the case of compounds 28 and 776 (which would fall under Structure IA; and are discussed in more detail below), excellent activity is seen where the amino acid derived side chain (alanine) contains both the R (28) and S (776) configurations. In these cases, while not being limited to theory, specific activity among isomers is determined by the unique structural elements within the molecule in addition to the exact stereochemistry. While it is known that molecules having the right balance of hydrogen bonding groups (i.e. —NHR, —OH, —CONHR, etc.), Log P value, and molecular weight range are preferred, unique structural elements can contribute to activity within these preferred ranges. The current compounds of interest contain polar groups in the side-chain which are capable of both hydrogen bonding and balancing the lipophilicity of the overall structure. The stereochemical features within these molecules also impart a 3D dimensionality to the structure which can enhance interaction with specific receptors. It is believed that these unique structural features lead to enhanced affinity for the receptor which translates into the prolonged cooling effects which have been observed.

It has been discovered that cyclohexanecarboxamide, 5-methyl-2-(1-methylethyl)-N-(2-phenylethyl)-, (1R,2S,5R) (CAS#824947-52-6) and cyclohexanecarboxamide, 5-methyl-2-(1-methylethyl)-N-(2-phenylethyl)-, (1R,2S,5R) (CAS#847564-71-0) structures (shown above) with 2-amino-propanamide (CAS#4726-84-5) have enhanced long lasting cooling properties and cyclohexanecarboxamide, 5-methyl-2-(1-methylethyl)-N-phenyl-, (1R,2S,5R) and cyclohexanecarboxamide, 5-methyl-2-(1-methylethyl)-N-1-naphthalenyl-(1R,2S,5R) (CAS#863091-95-6) structures with an aminoethane (CAS#75-04-7) moiety deliver a warming sensation. Both types of cyclohexanecarboxamide (cooling and warming) are efficacious at low use levels (1-10 ppm). The advantage of using such low levels of these materials allows for their formulation into higher water compositions, such as mouthrinses, without the need for additional processing aids, such as co-surfactants, oils, or other suspension agents. These materials may also provide mitigation of off tasting sensations, such as that derived from metal salts, peroxide, and CPC.

Other suitable uses for long lasting TRPM8 activity as exemplified from compound 28, would be for food applications; skin conditions, such as treatments for non-keratinzed stratified epithelium; analgesic applications as pain mitigation agents; reductions in inflammation; additives to cigarettes; topical salves for muscle pain, for chronic pain from osteoarthritis, and for chemotherapy induced neuropathy; skin barrier recovery accelerants; and antipruritic or antiseptic medications; and for vasoconstriction in relaxed vessels.

The levels of use for compounds of the present invention, such as compound 28, depend upon the targeted TRPM8 area of the body. For example when a compound of the present invention is used in a medication composition that dissolves in a user's mouth, such as a lozenge or a dissolvable strip, the levels of use may be from about 0.00001% to about 0.1% by weight of the composition; from about 0.00005% to about 0.1% by weight of the composition; from about 0.0001% to about 0.05% by weight of the composition; or from about 0.001% to about 0.01% by weight of the composition. In another example, when a compound of the present invention is used in a liquid medication composition, the level of use may be from about 0.000001% to about 0.01% by weight of the composition; from about 0.00001 to about 0.005% by weight of the composition; from about 0.00005% to about 0.001% by weight of the composition; from about 0.0005% to about 0.005% by weight of the composition; or from about 0.0001% to about 0.001% by weight of the composition. In another example, when a compound of the present invention is used in an inhalable composition, such as a nasal spray or a vapor inhaler, the level of use may be from about 0.0000001% to about 0.010% by weight of the composition; from about 0.001001 to about 0.0005% by weight of the composition; from about 0.000005% to about 0.0001% by weight of the composition; from about 0.00005% to about 0.0005% by weight of the composition; or from about 0.00001% to about 0.0001% by weight of the composition. In another example, when a compound of the present invention is a coated solid dosage form, the level of use in the coating may be from about 0.00001% to about 0.1% by weight of the composition; from about 0.0001 to about 0.05% by weight of the composition; from about 0.0005% to about 0.01% by weight of the composition; from about 0.005% to about 0.05% by weight of the composition; or from about 0.001% to about 0.01% by weight of the composition. When a compound of the present invention, such as compound 28, is delivered topically, for example in topical ointments, the levels may be from about 0.0001% to about 1% by weight of the composition; from about 0.001% to about 0.8% by weight of the composition; from about 0.005% to about 0.7% by weight of the composition; from about 0.01% to about 0.5% by weight of the composition; from about 0.02% to about 0.3% by weight of the composition; or from about 0.05% to about 0.4% by weight of the composition.

The composition can contain a solvent. Non-limiting examples of solvents can include water, ethanol, glycerol, propylene glycol, polyethylene glycol 400, polyethylene glycol 200, and mixtures thereof. In one example the medication comprises from about 40% to about 95% solvent, in another example from about 50% to about 80% solvent, and in another example from about 55% to about 60% solvent, and in another example from about 68% solvent to about 72% solvent.

In one example, the medication can contain water and propylene glycol. In one example, the medication comprises from about 15% to about 80% water, in another example from about 25% to about 75% water, in another example from about 40% to about 70% water, in another example from about 35% to about 45% water, and in another example from about 57% to about 66% water. In another example, the medication can contain from about 1% to about 10% propylene glycol, in another example from about 2% to about 8% propylene glycol, and in another example from about 3% to about 6% propylene glycol. In another example, the medication can contain from about 5% to about 40% propylene glycol, in another example from about 15% to about 35% propylene glycol, and in another example from about 20% to about 30% propylene glycol. In another example, the medication can comprise from about 1% to about 15% ethanol, in another example from about 3% to about 12% ethanol, and in another example from about 6% to about 10% ethanol.

The compositions can comprise a sweetener to provide sweetness and taste masking of the actives and excipients that provide a bitter character. In one example, the composition comprises from about 2% to 25% sweetener, in another example from about 5% to 20% sweetener, in another example from about 7% to 15% sweetener, and in another example from about 8% to 12% sweetener. Non-limiting examples of sweeteners can include nutritive sweeteners, sugar alcohols, synthetic sugars, high intensity natural sweeteners, and combinations thereof. Non-limiting examples of nutritive sweeteners can include fructose, galactose, and combinations thereof. In one example, the sweetener can be high fructose corn syrup.

Non-limiting examples of sugar alcohols can include xylitol, sorbitol, mannitol, maltitol, lactitol, isomalt, erthritol, glycerin, and combinations thereof. In one example the composition can comprise from about 1% to about 30% sugar alcohol, in another example from about 5% to about 28% sugar alcohol, in another example about 10% to about 25% sugar alcohol, and in another example about 15% to about 23% sugar alcohol. In one example the composition comprises from about 5% to about 20% sorbitol, in another example from about 7% to about 18% sorbitol, and in another example from about 10% to about 15% sorbitol. In another example, the composition comprises from about 3% to about 15% glycerin, in another example from about 5% to about 10% glycerin, and in another example from about 7% to about 9% glycerin.

Non-limiting examples of synthetic sweeteners can include sodium saccharin, acesulfame potassium, sucralose, aspartame, monoammonium glycyrrhizinate, neohesperidin dihydrochalcone, thaumatin, neotame, cyclamates, and mixtures thereof. In one example the composition can comprise from about 0.01% to about 0.5% artificial sweetener, in another example from about 0.1% to about 0.3% artificial sweetener, and in another example about 0.15% to about 0.25% artificial sweetener.

Non-limiting examples of high intensity natural sweeteners can include neohesperidin dihydrochalcone, stevioside, rebaudioside A, rebaudioside C, dulcoside, monoammonium glycrrhizinate, thaumatin, and combinations thereof.

The composition can comprise a flavoring ingredient. When present, flavoring ingredients are generally used in the compositions at levels of from about 0.001% to about 8%, by weight of the composition.

Additional non-limiting examples of flavoring ingredients can include peppermint oil, corn mint oil, spearmint oil, oil of wintergreen, clove bud oil, *cassia*, sage, parsley oil, marjoram, lemon, lime, orange, mango, cis-jasmone, 2,5-dimethyl-4-hydroxy-3(2H)-furanone, 5-ethyl-3-hydroxy-4-methyl-2(5H)-furanone, vanillin, ethyl vanillin, propenyl guaethol, heliotropine, 4-cis-heptenal, diacetyl, methyl-p-tert-butyl phenyl acetate, menthol, methyl salicylate, ethyl salicylate, 1-menthyl acetate, oxanone, alpha-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, alpha-terpineol, linalool, limonene, citral, maltol, ethyl maltol, carvone, menthone, β-damascenone, ionone, gamma decalactone, gamma nonalactone, gamma undecalactone and mixtures thereof. Generally suitable flavoring ingredients are those containing structural features and functional groups that are less prone to redox reactions. These include derivatives of flavouring ingredients that are saturated or contain stable aromatic rings or ester groups. In one example, the composition comprises from about 0.01% to about 1% flavoring ingredients, in another example from about 0.05% to about 0.5% flavoring ingredients, and in another example from about 0.1% to about 0.3% flavoring ingredients.

In one example, the composition can be a topical ointment containing from about 0% to about 2.6% menthol, in another example from about 0.5% to about 2.0%, in another example from about 1.0% to about 1.7%, and in another example from about 1.3% to about 1.5%. In another example, the composition does not contain menthol. In another example, the composition contains less than 2.6% menthol and is at least equally preferred by consumers to Vicks® VapoRub® (commercially available April 2015).

In one example, the composition can be a vapor inhaler containing from about 0% to about 60% menthol, in another example from about 20% to about 55%, in another example from about 27% to about 50%, and in another example from about 35% to about 45%. In another example, the composition does not contain menthol. In another example, the composition contains less than 40% menthol and is at least equally preferred by consumers to commercially available vapo inhalers (commercially available April 2015).

The composition can be any color. Non-limiting examples of colors can include red, green, amber, orange, yellow, blue, pink, violet, turquoise, and combinations thereof. In one example, the composition is green. In another example, the composition is clear.

The composition can also comprise a dye that provides the color. Non-limiting examples dyes that may be used in the present invention include FD&C blue #1, FD&C blue #2, D&C blue #4, D&C blue #9, FD&C green #3, D&C green #5, D&C green #6, D&C green #8, D&C orange #4, D&C orange #5, D&C orange #10, D&C orange #11, FD&C red #3, FD&C red #4, D&C red #6, D&C red #7, D&C red #17, D&C red #21, D&C red #22, D&C red #27, D&C red #28, D&C red #30, D&C red #31, D&C red #33, D&C red #34, D&C red #36, D&C red #39, FD&C red #40, D&C violet #2, FD&C yellow #5, FD&C yellow #6, D&C yellow #7, Ext. D&C yellow #7, D&C yellow #8, D&C yellow #10, D&C yellow #11, and combinations thereof. In one example, the composition comprises from about 0.001% to about 0.1% dye, in another example from about 0.002% to about 0.05% dye, and in another example form about 0.003% to about 0.01% dye.

In one example, the composition comprises a buffer. The buffer can help maintain a constant pH within the composition. In one example the composition comprises from about 0.05% to about 2% buffer, in another example from about 0.1% to about 1% buffer, in another example from about 0.15% to about 0.5% buffer, and in another example from about 0.18% to about 0.25% buffer. Buffers can include acetate buffers, citrate buffers, and phosphate buffers. Non-limiting examples of buffers can include acetic acid, sodium acetate, citric acid, sodium citrate, monobasic sodium phosphate, dibasic sodium phosphate, sodium carbonate, sodium bicarbonate, succinic acid, sodium succinate, potassium dihydrogen phosphate, and phosphoric acid.

In one example, the composition comprises a preservative. In one example the composition comprises from about 0.01% to about 1% preservative, in another example from about 0.05% to about 0.5% preservative, in another example from about 0.07% to about 0.3% preservative, and in another example from about 0.08% to about 0.15% preservative. Non-limiting examples of preservatives can include benzalkonium chloride, ethylenediaminetetraacetic acid (EDTA), benzyl alcohol, potassium sorbate, parabens, benzoic acid, sodium benzoate, and mixtures thereof.

In one example, the composition comprises a thickener. In one example the composition comprises from 0.01% to 3% thickener, in another example 0.05% to 1.5% thickener, in another example 0.1% to 0.75% thickener, and in another example 0.12% to 0.3% thickener. Non-limiting examples of thickeners can include xanthan gum, carrageenan, polyacrylic acid, polyvinylpyrrolidone, cellulosic polymers including carboxymethycellulose, hydroxethylcellulose, hydroxymethylcellulose, and hydroxypropylmethylcellulose, and combinations thereof.

The compositions can comprise one or more drug actives. In one example, the drug actives can be immediate release drug actives, extended release drug actives, or delayed release drug actives. In one example, the drug active can be formulated as particles and in another example the active can be formulated as coated beads.

In one example, the drug active is a MSR cold/flu active which can be used to treat one or more cold/flu symptoms. MSR cold/flu actives can be used to treat a variety of cold/flu symptoms including nasal congestion, runny nose, sneezing, headache, dry cough, sore throat, sinus pressure or pain, chest congestion, muscle aches/pains, wet/chesty cough, fever, and combinations thereof. MSR cold/flu actives can include decongestants, expectorants, antihistamines, antitussives, pain relievers, and combinations thereof.

In one example, MSR cold/flu actives can be formulated for daytime use or nighttime use. In one example, the liquid medication comprises instructions that direct a user to ingest the medication at night before bedtime.

Non-limiting examples of expectorants can include guaifenesin, ambroxol, bromhexine, and combinations thereof. In one example, the expectorant can be guaifenesin. In one example a dose can comprise 200 mg of guaifenesin and in another example 400 mg of guaifenesin.

Non-limiting examples of antihistamines can include chlorpheniramine, desloratadine, levocetirizine, diphenhydramine, doxylamine succinate, triprolidine, clemastine, pheniramine, brompheniramine, dexbrompheniramine, loratadine, cetirizine and fexofenadine, amlexanox, alkylamine derivatives, cromolyn, acrivastine, ibudilast, bamipine, ketotifen, nedocromil, omalizumab, dimethindene, oxatomide, pemirolast, pyrrobutamine, pentigetide, thenaldine, picumast, tolpropamine, ramatroban, repirinast, suplatast tosylate aminoalkylethers, tazanolast, bromodiphenydramine, tranilast, carbinoxamine, traxanox, chlorphenoxamine, diphenylpyaline, embramine, p-methyldiphenydramine, moxastine, orphenadrine, phenyltoloxamine, setastine, ethylenediamine derivatives, chloropyramine, chlorothen, methapyrilene, pyrilamine, talastine, thenyldiamine, thonzylamine hydrochloride, tripelennamine, piperazines, chlorcyclizine, clocinizine, homochlorcyclizine, hydroxyzine, tricyclics, phenothiazines, mequitazine, promethazine, thiazinamium methylsulfate, azatadine, cyproheptadine, deptropine, desloratadine, isothipendyl, olopatadine, rupatadine, antazoline, astemizole, azelastine, bepotastine, clemizole, ebastine, emedastine, epinastine, levocabastine, mebhydroline, mizolastine, phenindamine, terfenadine, tritoqualine, phenylephrine (PE), pseudoephedrine (PSE) and combinations thereof.

In one example the composition can comprise from about 0.01% to about 0.1% antihistamine, in another example from about 0.02% to about 0.07% antihistamine, and in another example from about 0.03% to about 0.05% antihistamine. In one example, the antihistamine can be doxylamine succinate and a dose of liquid medication can contain 12.5 mg doxylamine succinate. In another example, the antihistamine can be chlorpheniramine. In one example a dose can contain 2 mg of chlorpheniramine and in another example a dose can contain 4 mg of chlorpheniramine. In another example, the antihistamine can be PE. In one example a dose can contain 5 mg PE, in another example 10 mg PE, and in another example 20 mg PE. In another example, the antihistamine can be PSE. In one example a dose can contain 120 mg PSE and in another example 30 mg PSE.

Non-limiting examples of antitussives can include DXM, codeine, chlophedianol, levodropropizine, and combinations thereof. In one example the liquid medication can comprise from about 0.01% to about 0.2% antitussive, in another example from about 0.025% to about 0.1%, and in another example from about 0.04% to about 0.075% antitussive. In one example the antitussive can be selected from the group consisting of DXM, chlophedianol, and combinations thereof. In one example a dose can comprise 15 mg DXM, in another example 20 mg DXM, and in another example 30 mg DXM. In another example a dose can comprise 12.5 mg chlophedianol.

Non-limiting examples of pain relievers can include APAP, ibuprofen, ketoprofen, diclofenac, naproxen, aspirin, and combinations thereof. In one example the liquid medication can comprise from about 0.5% to about 3.5% pain reliever, in another example from about 1% to about 3% pain reliever, and in another example from about 1.5% to about 2% pain reliever. In one example the pain relievers can include APAP, ibuprofen, naproxen, or combinations thereof. In one example a dose can comprise 325 mg to 500 mg APAP, in another example 200 mg ibuprofen, and in another example, 200 mg naproxen.

In one example, the liquid medication can further comprise a stimulant such as caffeine.

In one example, the liquid medication can comprise one or more MSR cold/flu actives, in another example two or more MSR cold/flu actives, in another example three or more MSR cold/flu actives, and in another example four or more MSR cold/flu actives. In one example, the liquid medication can comprise exactly one MSR cold/flu active, in another example exactly two MSR cold/flu actives, in another example exactly three MSR cold/flu actives, and in another example exactly four MSR cold/flu actives. In one example the liquid medication can comprise APAP, doxylamine succinate, DXM, and PE.

In one example, the active can be a plant-derived materials. As used herein, non-limiting examples of plant-derived materials can include those used in traditional native American, Chinese, Aryuvedic and Japanese medicine, including flowers, leaves, stems and roots of plants as well as extracts and isolated active components from the flower, leaves, stems, and roots of plants. Plant and Animal based oils and esters such as Omega-3-fatty acids and alkyl esters thereof; Vitamins (including but not limited to provitamin and all forms of Vitamins C, D, A, B, E, and combinations thereof). Fibers: Non-limiting examples of fibers and analogous carbohydrate polymers can include pectins, *psyllium*, guar gum, xanthan gum, alginaes, gum arabic, fructo-oligosaccharides, inulin, agar, beta-glucans, chitins, dextrins, lignin, celluloses, non-starch polysaccharides, carrageenan, reduced starch, and mixtures and/or combinations thereof; Prebiotics: Non-limiting examples of prebiotics suitable for use in the compositions and methods can include *psyllium*, fructo-oligosaccharides, inulin, oligofructose, galacto-oligosaccharides, isomalto-oligosaccharides, xylo-oligosaccharides, soy-oligosaccharides, gluco-oligosaccharides, mannan-oligosaccharides, arabinogalactan, arabinxylan, lactosucrose, gluconannan, lactulose, polydextrose, oligodextran, gentio-ligosaccharide, pectic oligosaccharide, xanthan gum, gum arabic, hemicellulose, resistant starch and its derivatives, reduced starch, and mixtures and/or combinations thereof. Probiotics: Non-limiting examples of probiotic bacteria suitable for use herein can include strains of *Streptococcus lactis, Streptococcus cremoris, Streptococcus diacetylactis, Streptococcus thermophilus, Lactobacillus bulgaricus, Lactobacillus acidophilus, Lactobacillus helveticus, Lactobacillus bifidus, Lactobacillus casei, Lactobacillus lactis, Lactobacillus plantarum, Lactobacillus rhamnosus, Lactobacillus delbruekii, Lactobacillus thermophilus, Lactobacillus fermentii, Lactobacillus salivarius, Lactobacillus reuteri, Lactobacillus brevis, Lactobacillus paracasei, Lactobacillus gasseri, Pediococcus cerevisiae, Bifidobacterium longum, Bifidobacterium infantis, Bifidobacterium adolescentis, Bifidobacterium bifidum, Bifidobacterium animalis, Bifidobacterium pseudolongum, Bifidobacterium thennophilum, Bifidobacterium lactis, Bifidobacterium bulgaricus, Bifidobacterium breve, Bifidobacterium subtilis, Escherichia coli* and strains of the genera including *Bacillus, Bacteroides, Enterococcus* (e.g., *Enterococcus faecium*) and *Leuconostoc*, and mixtures and/or combinations thereof.

Minerals, metals and/or elements: Non-limiting examples of minerals, metals, and elements useful in the systems of the present invention include: zinc, iron, calcium, iodine, copper and selenium. When present, the minerals, metals and/or elements can be on or in a suitable carrier, and comprise from about 1% to about 50% by weight and alternatively from about 2% to about 30%, by weight of the composition comprising the mineral, metal or element and the carrier.

In another example, the active can be a gastrointestinal active. Non-limiting examples of gastrointestingal actives can include anti-diarrheal actives, laxatives, anti-nausea and anti-emetic actives, anti-flattulents, proton pump inhibitors, anti-inflammatory gastrointestinal actives, rafting agents, and combinations thereof.

Non-limiting examples of anti-diarrheal actives can include loperamide, bismuth-containing compositions, bismuth subsalicylate, colloidal bismuth subcitrate, bismuth subcitrate, kaolin, pectin, clays such as attapulgite, activated charcoal, and combinations thereof.

Non-limiting examples of laxatives can include fiber, resistant starch, resistant maltodextrin, pectin, cellulose, modified cellulose, polycarophil, *senna*, sennosides, bisacodyl, sodium phosphate, docusate, magnesium citrate, mineral oil, glycerin, aloe, castor oil, magnesium hydroxide, and combinations thereof.

Non-limiting examples of anti-nausea and anti-emetic actives can bismuth containing compositions including bismuth subsalicylate, phosphated carbohydrates, diphenhydramine, cyclizine, meclizine, and combinations thereof; non-limiting examples of antacids can include sodium bicarbonate, sodium carbonate, calcium carbonate, magnesium carbonate, magnesium hydroxide, aluminum hydroxide, magnesium silicates, alginic acids, sodium alginate, magaldrate, and combinations thereof.

Non-limiting examples of anti-flattulents can include simethicone, activated charcoal, lactase, alpha-galactosidase enzymes, and combinations thereof; non-limiting examples of H2 receptor antagonists can include famotidine, ranitidine, ciemtidine, nitazidine, and combinations thereof.

Non-limiting examples of proton pump inhibitors can include omeprazole, lansoprazole, esomeprazole, pantoprazole, rabeprazole, and combinations thereof.

A non-limiting example of an anti-inflammatory gastrointestinal active can include mesalamine.

Non-limiting examples of rafting agents can include alginates, pectins and polysaccharides.

EXAMPLES

Example 1

To determine what effect, if any, test compounds (shown in TABLE 1) had on TRPM8 (SEQ ID NO: 3), TRPA1 (SEQ ID NO: 2), and TRPV1 (SEQ ID NO: 1) activation the protocols listed below were used.

TRPM8 Protocol-FLIPR Assay

To determine whether TRPM8 is activated, the intracellular calcium ion ($Ca^{2+}$) level was measured from transfected cells with the TRPM8 receptor sequence (SEQ ID NO: 3). HEK-293 (human embryonic kidney) cells stably transfected with human TRPM8 were grown in 15 ml growth medium (high glucose DMEM (Dulbecco's Modification of Eagle's Medium) supplemented with 10% FBS (fetal bovine serum), 100 ug/ml penicillin/streptomycin, 5 µg/ml blasticindin, and 100 µg/ml zeocin) in a 75 cm² flask for 3 days at 37° C. in a mammalian cell culture incubator set at 5% $CO_2$ Cells were detached with addition of 2 ml of trypsin-EDTA buffer (GIBCO® 25200, Invitrogen, Grand Island, N.Y.) for about 2-3 min. Trypsin was inactivated by addition of 8 ml growth medium. Cells were transferred to a 50 ml tube and centrifuged at 850 rpm for 3 minutes to remove medium. After centrifugation, a pellet of cells was formed in the bottom of the tube separating them from the supernatant solution. The supernatant was discarded and the cell pellet was suspended in 1 ml of fresh growth medium to which 5 µl (12.5 µg) of Fluo-4 AM (Molecular Probes, Inc., Eugene, Oreg.) calcium indicator was added and incubated for 30 min with gentle shaking. Fluo-4 AM is a fluorescent dye used for quantifying cellular $Ca^{2+}$ concentrations in the 100 nM to 1 microM range. At the end of 30 minutes, 45 ml of assay buffer (1×HBSS (Hank's Balanced Salt Solution), 20 mM HEPES (4-(2-Hydroxyethyl)-1-piperazineethanesulfonic acid)) was added to wash cells and the resulting mixture was then centrifuged at 850 rpm for 3 minutes to remove excess buffer and Fluo-4 AM calcium indicator.

The pelleted cells were re-suspended in 10 ml assay buffer and 90 µl aliquots (~50,000 cells) per well delivered to a 96-well assay plate containing 10 µl of test compounds (1 mM in assay buffer, final concentration 100 µM) or buffer control and incubated at room temperature for 30 minutes. After 30 minutes, a plate was placed into a fluorometric imaging plate reader (FLIPR384 from Molecular Devices, Sunnyvale, Calif.) and basal fluorescence recorded (excitation wave length 488 nm and emission wave length 510 nm). Then 20 µl of 100 mM of TRPM8 agonist WS5 coolant in the assay buffer was added and fluorescence recorded. For determining the direct effect of test compounds on TRPM8, fluorescence was measured immediately after addition of each compound (TABLES 2 and 3). Additional discussion of the FLIPR method can be found in Smart et al., Characterization using FLIPR of human vanilloid VR1 receptor pharmacology, European Journal of Pharmacology 417, 51-58 (2001) and Liu et al., Development and validation of a platelet calcium flux assay using a fluorescent imaging plate reader, Analytical Biochemistry 357, 216-224 (2006).
TRPA1 Protocol—FLIPR Assay To determine whether TRPA1 is activated, the intracellular calcium ion ($Ca^{2+}$) level from transfected cells with the TRPA1 receptor sequence (SEQ ID NO: 2) was measured. HEK-293 cells stably transfected with human TRPA1 were grown in 15 ml growth medium (high glucose DMEM (Dulbecco's Modification of Eagle's Medium) supplemented with 10% FBS (fetal bovine serum), 100 µg/ml penicillin/streptomycin, 100 µg/ml G418) in a 75 cm² flask for 3 days at 37° C. in a mammalian cell culture incubator set at 5% $CO_2$. Cells were detached with addition of 10 ml of PBS (phosphate buffered saline) by hand shaking gently and transferred to a 50 ml tube and centrifuged at 850 rpm for 3 minutes to remove PBS. After centrifugation, a pellet of cells was formed in the bottom of the tube separating them from the supernatant solution. The supernatant was discarded and the cell pellet suspended in 1 ml of fresh growth medium to which 5 µl (12.5 µg) of Fluo-4 AM (Molecular Probes, Inc.) calcium indicator was added and incubated for 30 minutes with gentle shaking. At the end of the 30 minutes, 45 ml of assay buffer (1×HBSS (Hank's Balanced Salt Solution), 20 mM HEPES (4-(2-Hydroxyethyl)-1-piperazineethanesulfonic acid)) was added to wash the cells and the resulting combination was then centrifuged at 850 rpm for 3 minutes to remove excess buffer and Fluo-4 AM calcium indicator.

The pelleted cells were re-suspended in 10 ml assay buffer and 90 µl aliquots (50,000 cells) per well delivered to a 96-well assay was placed into a fluorometric imaging plate reader (FLIPR TETRA from Molecular Devices) and basal fluorescence recorded (excitation wave length 488 nm and emission wave length 510 nm). Then 20 µl of the test compound being tested was added and fluorescence recorded (TABLES 2 and 3).

To determine if a compound was an agonist the direct effect of a test compound was determined. If any increase in fluorescence over background was noted, then the compound was considered an agonist. The agonist activity was expressed relative to that observed with a benchmark agonist such as 50 µM allyl isothiocyanate for TRPA1.
TRPV1 Protocol—FLIPR Assay To determine whether TRPV1 was activated, the intracellular calcium ion ($Ca^{+2}$) levels from cells transfected with the TRPV1 receptor sequence (SEQ ID NO: 1) were measured. HEK-239 cells stably transfected with human TRPV1 were grown in 15 ml growth medium (high glucose DMEM (Dulbecco's Modification of Eagle's Medium) supplemented with 10% FBS (fetal bovine serum), 100 µg/ml Penicillin/streptomycin, 100 µg/ml G418) in a 75 cm² flask for 3 days at 33° C. in a mammalian cell culture incubator set at 5% $CO_2$. Cells were detached with addition of 10 ml of PBS (phosphate buffered saline) by gentle hand shaking. Cells were transferred to a 50 ml tube and centrifuged at 850 rpm for 3 minutes to remove PBS. After centrifugation, a pellet of cells formed in the bottom of the tube separating them from the supernatant solution. The supernatant was discarded and the cell pellet suspended in 1 ml of fresh growth medium to which 5 µl (12.5 µg) of Fluo-4 AM (Molecular Probes, Inc., Eugene, Oreg.) calcium indicator was added and incubated for 30 minutes with gentle shaking. At the end of the 30 minutes, 45 ml of assay buffer (1×HBSS (Hank's Balanced Salt Solution), 20 mM HEPES (4-(2-Hydroxyethyl)-1-piperazineethanesulfonic acid)) was added to wash the cells and the resulting combination was then centrifuged at 850 rpm for 3 minutes to remove excess buffer and Fluo-4 AM calcium indicator.

The pelleted cells were re-suspended in 10 ml assay buffer and 90 µl aliquots (50,000 cells) per well delivered to a 96-well assay plate was placed into a fluorometric imaging plate reader (FLIPR TETRA from Molecular Devices) and basal fluorescence recorded (excitation wave length 488 nm and emission wave length 510 nm). Then 20 µl of a test compound-being tested as a TRPV1 receptor agonist was added and fluorescence recorded. The observed value with compound pretreated cells was compared with buffer control; the difference between the two indicating a measure of effect of the test compound on the agonist (TABLES 2 and 3).

If any increase in fluorescence over background was noted, then the compound was considered an agonist. The agonist activity was expressed relative to that observed with a benchmark agonist such as 350 nM Capsaicin for TRPV1.

TABLE 1

Test Compounds

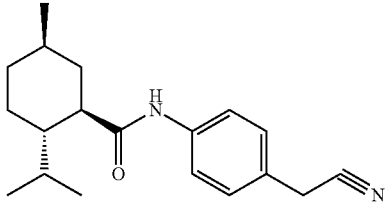

Cyclohexane-carboxamide, N-
[4-(cyanomethyl)
phenyl]-5-methyl-2-(1-
methylethyl)-,
(1R,2S,5R)—— 180

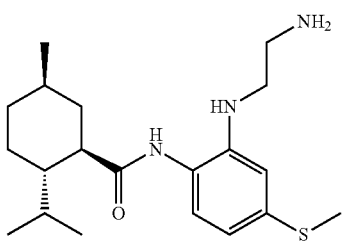

Cyclohexanecarboxamide
N-[2-[(2-aminoethyl)amino]-4-
(methylthio)phenyl]-5-
methyl-2-(1-methylethyl)-
(1R,2S,5R)——* 773

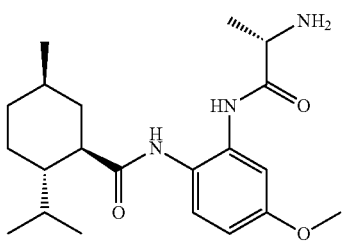

Cyclohexanecarboxamide,
N-[2-[[(2S)-2-amino-1-
oxopropyl]amino]-4-
methoxyphenyl]-
5-methyl-2-(1-
methylethyl)-,
(1R,2S,5R)——* 776

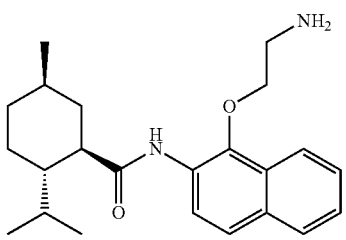

Cyclohexanecarboxamide,N-[1-
(2-aminoethoxy)-2-naphthalenyl]-
5-methyl-2-(1-methylethyl)-,
(1R,2S,5R)* 777

TABLE 1-continued

Test Compounds

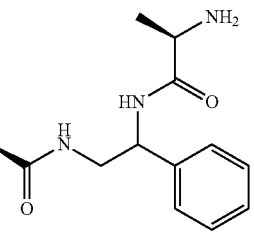

Cyclohexanecarboxamide, N-[2-
[[(2R)-2-amino-1-oxopropyl]
amino]-2-phenylethyl]-
5-methyl-2-(1-methylethyl)-,
(1R,2S,5R)——* 28

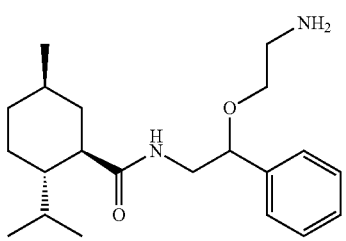

Cyclohexanecarboxamide,
N-[2-(2-aminoethoxy)-
2-phenylethyl]-5-methyl-
2-(1-methylethyl)-,
(1R,2S,5R)——* 30

TABLE 2

| Concentration Tested on HEK 293 receptor expressing cells | | | |
|---|---|---|---|
| Concentration of each test compound | TRPM8 | TRPA1 | TRPV1 |
| 180 | 0.001% | 0.001% | 0.001% |
| 773 | 0.004% | 0.02% | 0.02% |
| 776 | 0.004% | 0.02% | 0.02% |
| 777 | 0.004% | 0.02% | 0.02% |
| 28 | 5.2E–6% | 5.2E–5% | 5.2E–5% |
| 30 | 5.2E–5% | 5.2E–5% | 5.2E–5% |
| WS5 | 30 microMolar | — | — |
| Allyl Isothiocyanate (AITC) | — | 50 microMolar | — |
| Capsaicin | — | — | 350 nanoMolar |

TABLE 2 illustrates the concentration of each test compound when it was tested across the HEK 293 receptor containing cells.

TABLE 3

| Receptor Activity | | | |
|---|---|---|---|
| Tested Compounds | TRPM8 | TRPA1 | TRPV1 |
| 180 | 108.80% | 68.02% | 0.01% |
| 773 | 141.07% | 198.79% | 92.07% |
| 776 | 139.41% | 112.99% | 94.61% |
| 777 | 139.37% | 173.88% | 60.5% |
| 28 | 130.42% | 242.50% | 104.50% |
| 30 | 109.70% | 38.18% | 16.24% |

TABLE 3-continued

| | Receptor Activity | | |
|---|---|---|---|
| Tested Compounds | TRPM8 | TRPA1 | TRPV1 |
| WS5 | 100% | — | — |
| Allyl Isothiocyanate (AITC) | — | 100% | — |
| Capsaicin | — | — | 100% |

TABLE 3 showed the cell based receptor activity across the three receptors (TRPM8, TRPA1, and TRPV1). Compound 28 had surprisingly high activity across all three receptors, indicating it could deliver a variety of sensations depending on the concentration, when tested in vivo.

TABLE 3 shows the impact of each structure on the following receptors: TRPM8 (cooling); TRPA1 (burning, numbing, tingling, irritation); and TRPV1 (warming). The intensity of the described test compound across three receptors (TRPM8, TRPA1, and TRPV1) was compared to that of the control test compounds (WS5 for TRPM8, Allyl Isothiocyanate for TRPA1, and Capsaicin for TRPV1). The aminoethane moiety on compounds 773 and 777 directed the underlying phenyl cyclohexanecarboxamide to shift from perceived cooling to burning (high TRPA1 activity from 777) and warming (high TRPV1 activity from 773). Further, the potency of compound 28 relative to other carboxamide structures is illustrated from TABLES 2 and 3. For instance, at a screening level of 0.0000052% compound 28 delivered 130% of WS5 activity and WS5 was tested at 0.003%. N-(4-cyanomethylphenyl)-p-menthanecarboxamide was tested at 0.001% to get to 109% of WS5 activity. Therefore, at a single concentration, compound 28 is 100× more mass efficient than the next best coolant in class, N-(4-cyanomethylphenyl)-p-menthanecarboxamide. The EC50 values, as discussed later, show it is even more mass efficient as it is diluted, since it retains high activity at very low use levels.

Compounds 28 and 30 show additional structures with the aforementioned moieties 2-amino-propanamide adjacent to a phenyl ring for cooling; and ethanolamine adjacent to a phenyl ring for warming and/or burning sensations. When the aminoethane is off a phenyl ring, the sensorial component of the molecule appeared to diminish, as shown by the lack of sensation, cooling or warming, from test compound 30. The aminoethane (test compound 777) on a naphthalene moiety delivered a burning sensation. Compound 28 was highly potent on activation of the TRPM8 receptor as shown in TABLE 3 and in the reported cooling sensations by the panelists.

Example 2

Isomer Characterization of Compound 28

Two fractions of compound 28, as discussed below, were collected in gram quantities. The isomeric content of these two compound 28 fractions was characterized by LC-UV-MS using a Waters Acuity H Class, Ultra Performance Liquid Chromatograph (UPLC), equipped with the Sample Manager, Quaternary Solvent Manager, Tunable Ultraviolet (TUV) detector, and a QDa mass selective, single-quadrupole mass analyzer (Waters Corporation, Milford, Mass.). To prepare for analysis and characterization, a solid sample of each fraction was weighed and dissolved at approximately 100 μg/mL in a solution consisting of 50% deionized water/50% methanol (MeOH, HPLC grade from EMD Millipore Corporation, Billerica, Mass.) and also containing 0.1% trifluoroacetic acid (TFA, Sigma Aldrich Corporation, St. Louis, Mo.).

The separation of isomers contained within each fraction of compound 28 was achieved with a 2.1×100 mm Acuity UPLC BEH Shield RP18 column with 1.7 μm particles (Waters Corporation, Milford, Mass.). A mobile phase gradient was utilized with mobile phase (A) consisting of water plus 0.1% TFA from Sigma Aldrich, and mobile phase (B) consisting of MeOH from EMD. The mobile phase composition was equilibrated prior to injection at 75% (A)/25% (B) and, following a 5 sample injection, the mobile phase composition was ramped linearly to 100% (B) at 10 minutes. 100% of mobile phase (B) was held for 3 minutes before ramping back to the original conditions in 2 minutes. A mobile phase flow rate of 0.4 mL/minute was maintained throughout. UV traces were obtained by monitoring detector absorbance at 215 nm. QDa positive ion mass spectra of the peaks in the UV traces shown within FIGS. 1 to 3 displayed intense protonated molecular ions at m/z 374, as expected, given the structure of compound 28, and indicating the components highlighted within FIGS. 1 to 3 are isomeric species of compound 28.

Figure 2:
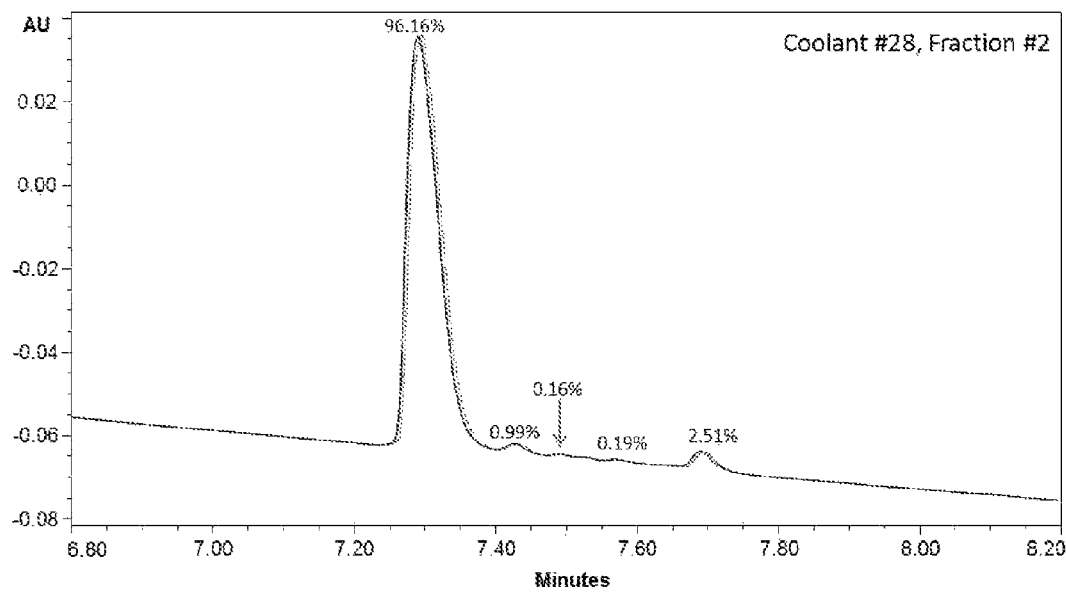
FIG. 2 UV chromatogram overlays of three replicate injections of compound 28, fraction 2. The percentages of relative peak areas are shown above for each isomeric compound observed within this mixture. All peaks appear at nominal m/z 374 in the QDa mass spectra, indicating that these are isomeric species. Fraction 2 has higher isomeric purity than fraction 1.

UV analysis of compound 28-fractions 1 and 2 are shown in FIGS. 1 and 2, respectively, indicating excellent retention time repeatability and a very good separation of the isomers found within these mixtures. FIG. 3 provides a UV overlay of a representative analysis from fraction 1 and fraction 2, highlighting the differences in isomeric composition for these two fractions of compound 28.

Figure 3:
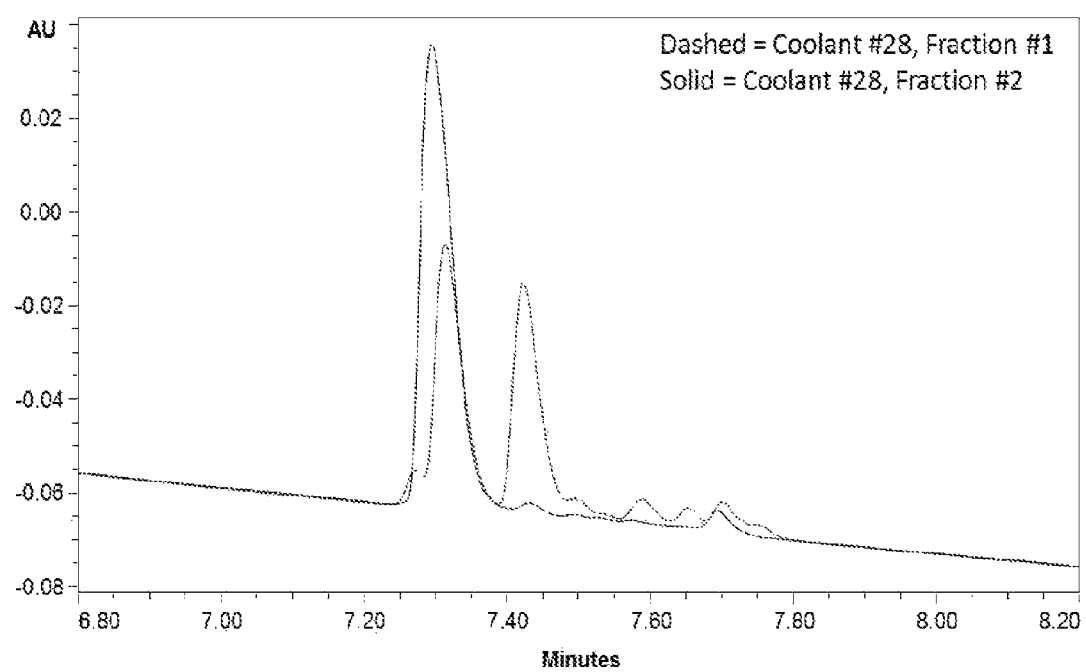
FIG. 3 UV trace overlays of chromatograms generated during separate analysis of compound 28, fraction 1 (dashed line) and fraction 2 (solid line). These overlays demonstrate that some components are contained within both fractions, while some components are essentially unique, and the ratio of isomers within these two fractions differ. All peaks appear at nominal m/z 374 in the QDa mass spectra, indicating that these are isomeric species.

FIG. 3 shows the HPLC of the isomers of compound 28. The fraction labeled fraction 1, collected at 7.4 to 7.5 minutes corresponds to the main isomer and lesser isomers that deliver the intense cooling and a low EC50 as determined from the TRPM8 activity as shown in TABLES 7, 8 and 9 below. The fraction labeled fraction 2, collected from 7.20 to 7.38 minutes corresponded to the isomers of compound 28 with much lower TRPM8 values, which did not provide a cooling response at the dose tested as shown in TABLES 7, 8 and 9.

TRPM8 activation was determined by measuring intracellular calcium ion ($Ca^{2+}$) level from transfected cells with the TRPM8 receptor gene, as described in EXAMPLE 1, the results of which are shown in TABLES 4 and 5.

TABLE 4

| TRPM8 Time Course Activity of compound 28 | | | | | | | | | |
|---|---|---|---|---|---|---|---|---|---|
| Sample | Dose | 50 sec | 50 sec % of WS5 | 3 min | 3 min % of WS5 | 5 min | 5 min % of WS5 | 10 min | 10 min % of WS5 |
| Assay Buffer | na | 0.0 | 0.0 | 0.0 | 0.0 | 0.0 | 0.0 | 0.0 | 0.0 |
| WS-5 | 30 uM | 10059.7 | 100.0 | 9449.3 | 100.0 | 9468.0 | 100.0 | 9576.0 | 100.0 |
| Compound 28 fraction 1 | 100 uM | 12646.0 | 125.7 | 12520.0 | 132.5 | 12844.0 | 135.7 | 13187.0 | 137.7 |
| | 50 uM | 12419.0 | 123.5 | 12295.0 | 130.1 | 12654.0 | 133.7 | 13169.0 | 137.5 |
| | 25 uM | 13046.0 | 129.7 | 13020.0 | 137.8 | 13354.0 | 141.0 | 14341.0 | 149.8 |
| | 12.5 uM | 12430.0 | 123.6 | 12591.0 | 133.3 | 12997.0 | 137.3 | 13947.0 | 145.6 |

TABLE 4-continued

TRPM8 Time Course Activity of compound 28

| Sample | Dose | 50 sec | 50 sec % of WS5 | 3 min | 3 min % of WS5 | 5 min | 5 min % of WS5 | 10 min | 10 min % of WS5 |
|---|---|---|---|---|---|---|---|---|---|
| | 6.25 uM | 12229.0 | 121.6 | 12775.0 | 135.2 | 13098.0 | 138.3 | 14102.0 | 147.3 |
| | 3.125 uM | 11637.0 | 115.7 | 12602.0 | 133.4 | 12939.0 | 136.7 | 13850.0 | 144.6 |
| | 1.563 uM | 11114.0 | 110.5 | 12135.0 | 128.4 | 12499.0 | 132.0 | 13440.0 | 140.4 |
| | 781 nM | 9786.0 | 97.3 | 12182.0 | 128.9 | 12618.0 | 133.3 | 13661.0 | 142.7 |
| | 390 nM | 7592.0 | 75.5 | 11373.0 | 120.4 | 11968.0 | 126.4 | 13121.0 | 137.0 |
| | 195 nM | 5418.0 | 53.9 | 11037.0 | 116.8 | 11824.0 | 124.9 | 13046.0 | 136.2 |
| | 97.6 nM | 3963.0 | 39.4 | 9744.0 | 103.1 | 10711.0 | 113.1 | 12011.0 | 125.4 |
| | 48.8 nM | 2916.0 | 29.0 | 8017.0 | 84.8 | 8983.0 | 94.9 | 10224.0 | 106.8 |
| | 24.4 nM | 1936.0 | 19.2 | 6405.0 | 67.8 | 7593.0 | 80.2 | 8879.0 | 92.7 |
| | 12.2 nM | 3018.0 | 30.0 | 8783.0 | 93.0 | 9830.0 | 103.8 | 11065.0 | 115.5 |
| | 6.1 nM | 884.0 | 8.8 | 3452.0 | 36.5 | 4426.0 | 46.7 | 5375.0 | 56.1 |

TABLE 5

TRPM8 Time Course Activity of Isomer of compound 28

| Sample | Dose | 50 sec | 50 sec % of WS5 | 3 min | 3 min % of WS5 | 5 min | 5 min % of WS5 | 10 min | 10 min % of WS5 |
|---|---|---|---|---|---|---|---|---|---|
| Assay Buffer | na | 0.0 | 0.0 | 0.0 | 0.0 | 0.0 | 0.0 | 0.0 | 0.0 |
| WS-5 | 30 uM | 10059.7 | 100.0 | 9449.3 | 100.0 | 9468.0 | 100.0 | 9576.0 | 100.0 |
| Compound 28 fraction 2 | 100 uM | 12246.0 | 121.7 | 11826.0 | 125.2 | 12074.0 | 127.5 | 12287.0 | 128.3 |
| | 50 uM | 12648.0 | 125.7 | 12352.0 | 130.7 | 12644.0 | 133.5 | 13179.0 | 137.6 |
| | 25 uM | 12110.0 | 120.4 | 11993.0 | 126.9 | 12284.0 | 129.7 | 13140.0 | 137.2 |
| | 12.5 uM | 12415.0 | 123.4 | 12501.0 | 132.3 | 12801.0 | 135.2 | 13755.0 | 143.6 |
| | 6.25 uM | 12236.0 | 121.6 | 12644.0 | 133.8 | 12891.0 | 136.2 | 13793.0 | 144.0 |
| | 3.125 uM | 11757.0 | 116.9 | 12699.0 | 134.4 | 12937.0 | 136.6 | 13890.0 | 145.1 |
| | 1.563 uM | 11331.0 | 112.6 | 12663.0 | 134.0 | 12954.0 | 136.8 | 13892.0 | 145.1 |
| | 781 nM | 10428.0 | 103.7 | 12887.0 | 136.4 | 13091.0 | 138.3 | 14116.0 | 147.4 |
| | 390 nM | 8766.0 | 87.1 | 11955.0 | 126.5 | 12301.0 | 129.9 | 13026.0 | 136.0 |
| | 195 nM | 7287.0 | 72.4 | 11477.0 | 121.5 | 12007.0 | 126.8 | 12427.0 | 129.8 |
| | 97.6 nM | 5007.0 | 49.8 | 10101.0 | 106.9 | 10747.0 | 113.5 | 11375.0 | 118.8 |
| | 48.8 nM | 2502.0 | 24.9 | 7721.0 | 81.7 | 8488.0 | 89.6 | 9289.0 | 97.0 |
| | 24.4 nM | 2311.0 | 23.0 | 6441.0 | 68.2 | 7226.0 | 76.3 | 7848.0 | 82.0 |
| | 12.2 nM | 1814.0 | 18.0 | 5446.0 | 57.6 | 6224.0 | 65.7 | 6809.0 | 71.1 |
| | 6.1 nM | 1944.0 | 19.3 | 4350.0 | 46.0 | 4763.0 | 50.3 | 4844.0 | 50.6 |

The TRPM8 data shown in TABLES 4 and 5, where TABLE 4 corresponds to fraction 1 and TABLE 5 corresponds to fraction 2, compares the dose response of the two HPLC separations, of the isomers (fraction 1, fraction 2) of compound 28. As shown in TABLES 4 and 5, both fractions activate TRPM8 rapidly at 781 nM of each. However, fraction 1 continued to activate at lower and lower doses compared to fraction 2. Fraction 1 was 103.8% of the control at 5 minutes of activation from a 12.2 nM dose; whereas, fraction 2 at the same time point and dose was 65.7% of the control. At 10 minutes of activation, the 12.2 nM dose was 115.5% of the control for fraction 1 and 71.1% of the control for fraction 2. These differences in isomers were further illustrated in the EC50 values as shown in TABLE 6 below.

TABLE 6

EC50 Calculation of Isomer fractions

| EC50 in TRPM8 ($\mu$M) | 50 sec | 3 min | 5 min | 10 min |
|---|---|---|---|---|
| fraction 2 | 0.1972 | 0.05548 | 0.04567 | 0.0374 |
| fraction 1 | 0.3306 | 0.001476 | ~5.235E−008 | ~1.148E−007 |

In a composition of the present invention, such as liquid medications and solid oral dosage units, when compound 28 is split into isomers or combined, the levels of use may be from about 10% to about 70% of fraction 1 and about 10% to about 70% of fraction 2 or from about 30% to about 60% of fraction 1 and about 30% to about 60% of fraction 2. When compound 28, either isomer or combined isomers, is combined with a TRPA1 agonist, TRPV1 agonist, or both, the level of use of a TRPA1 or TRPV1 agonist would be in the range of about 0.001% to about 0.5% or from about 0.01% to about 0.2% by weight of the composition of either the TRPA1 or TRPV1 agonists, where both TRPA1 agonists and/or TRPV1 agonists may be added separately or simultaneously to the composition containing compound 28. When another TRPM8 agonist, in addition to compound 28, is used, the level of use of the additional TRPM8 agonist may be from about 0.001% to about 0.5% or from about 0.005% to about 0.3% by weight of the composition. If a TRPM8 enhancer is used, in addition to compound 28, it may be added in a range of from about 0.001% to about 0.2% or from about 0.005% to about 0.1% by weight of the composition. Compositions of the present invention may contain multiple TRPA1 and TRPV1 agonists in the ranges disclosed above to deliver the enhanced sensorial signal from compound 28.

In a topical application of a compound of the present invention, for example in topical ointments and sprays, and inhalers, when compound 28 is split into isomers or combined, the levels of use may be from about 10% to about 70% of fraction 1 and about 10% to about 70% of fraction 2 or from about 30% to about 60% of fraction 1 and about 30% to about 60% of fraction 2. When compound 28, either isomer or combined isomers, is combined with a TRPA1 and/or a TRPV1 agonist, the level of use of a TRPA1 or TRPV1 agonist may be in the range of from about 0.001% to about 0.5% or from about 0.01% to about 0.2% by weight of the composition of either of the TRPA1 or TRPV1 agonists, where both TRPA1 agonists and TRPV1 agonists may be added separately or simultaneously to the composition containing compound 28. When another TRPM8 agonist is used, in addition to compound 28, the level of use of the additional TRPM8 agonist may be from about 0.001% to about 0.5% or from about 0.005% to about 0.3% by weight of the composition. If a TRPM8 enhancer is used, in addition to compound 28, it may be used in levels of from about 0.001% to about 0.2% or from about 0.005% to about 0.1% by weight of the composition. The compositions may contain multiple TRPA1 and TRPV1 agonists in the ranges stated to deliver the enhanced sensorial signal from compound 28.

Example 4

Compound 28 Solubility

TABLE 7

Solubility Parameter Calculation

| Compound | Dispersion $(MPa)^{0.5}$ | Polarity $(MPa)^{0.5}$ | Hydrogen bonding $(MPa)^{0.5}$ | Total Solubility Parameter $(MPa)^{0.5}$ |
|---|---|---|---|---|
| Compound 28 | 17.8 | 5.6 | 9.0 | 20.7 |

TABLE 7 outlines the Hansen solubility parameters for compound 28 and its isomers (fraction 1, fraction 2), as outlined previously. These parameters help to identify which solvents would be a good candidate for making stock solutions of >5%. Due to the low level of use in oral care products, a typical stock solution of ~1% would be sufficient to deliver 1 to 10 ppm. Solvents for the higher (>5%) would utilize Hansen's sphere calculations and a sphere radius in the range of 5-6 would sufficiently identify solvents for the higher stock solutions. In the range of oral care use of stock solutions in the 1-5% range, solvents such as ethanol, menthol, carvone, anethol, benzyl alcohol, and the polyols commonly used in oral care products could be used to make a stock solution.

The following examples further describe and demonstrate using the coolant compounds described herein in medication compositions. The examples are given solely for the purpose of illustration and are not to be construed as limitations of the present invention, as many variations thereof are possible without departing from the spirit and scope of the invention. All exemplified amounts are concentrations by weight of the total composition, i.e., w/w percentages, unless otherwise specified.

Example 5

Liquid Medication with Actives

TABLE 8

| Liquid Medication | | | | | | | |
|---|---|---|---|---|---|---|---|
| | 5A | 5B | 5C | 5D | 5E | 5F | 5G |
| Water | Q.S. | Q.S. | Q.S. | Q.S. | Q.S. | Q.S. | Q.S. |
| Propylene glycol | 23.02 | 23.02 | 23.02 | 23.02 | 23.02 | 23.02 | 23.02 |
| APAP | 2.00 | 2.00 | 2.00 | 2.00 | 2.00 | 2.00 | 2.00 |
| DXM | 0.062 | 0.062 | 0.062 | 0.062 | 0.062 | 0.062 | 0.062 |
| Doxylamine succinate | 0.038 | 0.038 | 0.038 | — | — | — | — |
| PE | 0.031 | 0.031 | 0.031 | 0.031 | 0.031 | 0.031 | 0.031 |
| Flavor | 0.5 | 0.4 | 0.3 | 0.5 | 0.4 | 0.3 | — |
| Compound 28 fraction 1 | 0.0001 | 0.0001 | 0.0001 | 0.00005 | 0.00005 | 0.00005 | 0.00005 |
| Compound 28 fraction 2 | — | — | — | 0.00005 | 0.00005 | 0.00005 | 0.00005 |
| Dihydroanethole | — | — | — | 0.001 | 0.015 | 0.21 | 0.00025 |
| Xanthan gum | 0.15 | 0.15 | 0.15 | 0.15 | 0.15 | 0.15 | 0.15 |
| Sodium benzoate | 0.10 | 0.10 | 0.10 | 0.10 | 0.10 | 0.10 | 0.10 |
| Sodium citrate dihydrate | 0.20 | 0.20 | 0.20 | 0.20 | 0.20 | 0.20 | 0.20 |
| Citric acid | 0.22 | 0.22 | 0.22 | 0.22 | 0.22 | 0.22 | 0.22 |
| Sodium saccharin | 0.13 | 0.13 | 0.13 | — | — | — | 0.13 |
| Acesulfame Potassium | 0.080 | 0.080 | 0.080 | — | — | — | — |
| Sodium chloride | 0.50 | 0.50 | 0.50 | 0.50 | 0.50 | 0.50 | 0.50 |
| Dye | 0.0043 | 0.0043 | 0.0043 | 0.0043 | 0.0043 | 0.0043 | 0.0043 |
| Glycerin (96%) | 8.00 | 8.00 | 8.00 | 8.00 | 8.00 | 8.00 | 8.00 |
| Sorbitol (70%) | 13.15 | 13.15 | 13.15 | 13.15 | 13.15 | 13.15 | 13.15 |
| | 5H | 5I | 5J | 5K | 5L | 5M | 5N |
| Water | Q.S. | Q.S. | Q.S. | Q.S. | Q.S. | Q.S. | Q.S. |
| Propylene glycol | 23.02 | 23.02 | 23.02 | 23.02 | 23.02 | 23.02 | 23.02 |
| APAP | 2.00 | 2.00 | 2.00 | 2.00 | 2.00 | 2.00 | 2.00 |
| DXM | 0.062 | 0.062 | 0.062 | 0.062 | 0.062 | 0.062 | 0.062 |
| Doxylamine succinate | — | — | — | — | — | 0.038 | 0.038 |
| PE | 0.031 | 0.031 | 0.031 | 0.031 | 0.031 | 0.031 | 0.031 |
| Flavor | 0 | 0 | 0.055 | 0.11 | 0.21 | — | — |
| Compound 776 | 0.0001 | 0.0001 | 0.0001 | 0.001 | 0.001 | 0.001 | 0.001 |

TABLE 8-continued

| Liquid Medication | | | | | | | |
|---|---|---|---|---|---|---|---|
| Xanthan gum | 0.075 | 0 | 0.15 | 0.15 | 0.15 | — | — |
| 95% Ethanol (190 Proof) | — | — | — | — | — | — | 7.25 |
| Sodium benzoate | 0.10 | 0.10 | 0.10 | 0.10 | 0.10 | 0.10 | 0.10 |
| Sodium citrate dihydrate | 0.20 | 0.20 | 0.20 | 0.20 | 0.20 | 0.20 | 0.20 |
| Citric acid | 0.22 | 0.22 | 0.22 | 0.22 | 0.22 | 0.22 | 0.22 |
| Sodium saccharin | 0.13 | 0.13 | 0.13 | 0.13 | 0.13 | 0.13 | 0.10 |
| Sodium chloride | 0.50 | 0.50 | 0.50 | 0.50 | 0.50 | 0.50 | 0.50 |
| Dye | 0.0043 | 0.0043 | 0.0043 | 0.0043 | 0.0043 | 0.0043 | 0.0043 |
| Glycerin (96%) | 8.00 | 8.00 | 8.00 | 8.00 | 8.00 | 8.00 | 8.00 |
| Sorbitol (70%) | 13.15 | 13.15 | 13.15 | 13.15 | 13.15 | 13.15 | 13.15 |

*QS refers to the term quantum sufficit, meaning as much as suffices, where the remainder of the formula hole is filled with this substance.

Examples 5A-5N can be made according to the following procedure. DXM, APAP, and doxylamine succinate, if present, can be added to propylene glycol by mixing at an appropriate speed for at least five minutes. If the actives are not dissolved after five minutes then the solution can be warmed slightly and stirred until the actives dissolve. An appropriate mixing speed means that the solution is mixed quickly but it does not splash out of the container. Next the flavor, which can include the cooling compound (compound 776, compound 28 fraction 1, or compound 28 fraction 2), can be added to the solution and can be mixed for at least five minutes or until dispersed, whichever is later. Then, if alcohol is present, it can be added as a solvent to form the glycol premix. If alcohol is not present, xanthan gum can be added to the solution and mixed, for no less than five minutes, until dispersed, to form the glycol premix.

Next, the glycol premix can be added to the water. Then, the following components can be added to the solution in the following order: the buffers, which include citric acid and sodium citrate, sodium benzoate, dye, sodium chloride, PE, and the sweeteners, which can include sodium saccharin, acesulfame potassium, glycerin, and sorbitol. Each component can be added and incorporated into the solution before the next component can be added. The solution can be mixed until all of the ingredients are dissolved and the solution is homogenous.

In certain examples, the compositions of Example 5 can provide on-demand relief of certain cold/flu symptoms. This can be especially useful because there can be a lag between the time the user takes the medication and when the actives begin working. Upon contact, the composition can reduce the amount of coughing and/or alleviate a sore throat and/or provide at least some nasal decongestion. The compositions can also cool the mouth, which can be very pleasant, especially if the user has a fever. The compositions can be administered orally and can be swallowed.

Example 6

Liquid Medication without Actives

TABLE 9

| Liquid Medication | | | | | |
|---|---|---|---|---|---|
| | 6A | 6B | 6C | 6D | 6E |
| USP Water | Q.S. | Q.S. | Q.S. | Q.S. | Q.S. |
| Sucralose | 0.08 | 0.08 | 0.08 | 0.08 | 0.08 |
| Sodium CMC | 0.50 | 0.50 | 0.50 | 0.50 | 0.50 |

TABLE 9-continued

| Liquid Medication | | | | | |
|---|---|---|---|---|---|
| | 6A | 6B | 6C | 6D | 6E |
| Propylene Glycol, USP | 15.00 | 15.00 | 15.00 | 15.00 | 15.00 |
| Sodium Benzoate NF, FCC | 0.10 | 0.10 | 0.10 | 0.10 | 0.10 |
| Sorbitol | 10.00 | 10.00 | 10.00 | 10.00 | 10.00 |
| Polyoxyl 40 Stearate | 0.45 | 0.45 | 0.45 | 0.45 | 0.45 |
| Polyethylene Oxide, NF | 0.15 | 0.05 | 0.25 | — | — |
| Benzoic Acid, USP | 0.15 | 0.15 | 0.15 | 0.15 | 0.15 |
| Carbomer 956 | — | — | — | 0.15 | 0.15 |
| Flavor | 0.98 | 0.98 | 1.01 | 1.01 | 1.01 |
| Compound 28 - Fraction 1 | 0.00005 | 0.0001 | 0.0005 | 0.001 | — |
| Compound 28 - Fraction 2 | 0.00005 | — | 0.0005 | — | — |
| Compound 776 | — | — | — | — | 0.001 |

Examples 6A to 6E can be made according to the method described in Example 5. The compositions of Example 6 can reduce the amount of coughing and/or alleviate a sore throat and/or provide at least some nasal decongestion. The compositions can also cool the mouth, which can be very pleasant, especially if the user has a fever. In some examples, the composition can be swallowed and in other examples the compositions can be expectorated.

Example 7

Coating Containing a Coolant

The following example further describes the inclusion of these coolant compounds in the coating formulation of a solid dosage form, which can include a compressed tablet.

TABLE 10

Coating Containing a Coolant

| | 7A | 7B | 7C | 7D | 7E | 7F | 7G | 7H |
|---|---|---|---|---|---|---|---|---|
| HPMC (Hydroxy Propeyl Methyl Cellulose) | 15.0 | 15.0 | 15.0 | 15.0 | 0.0 | 0.0 | 0.0 | 0.0 |
| CMC (Carboxy Methyl Cellulose) | 0.0 | 0.0 | 0.0 | 0.0 | 7.5 | 7.5 | 7.5 | 7.5 |
| Plasticizer (Glycerine) | 3.0 | 3.0 | 3.0 | 3.0 | 3.0 | 3.0 | 3.0 | 3.0 |
| Comound 776 | 0.011 | 0.001 | 0.0 | 0.0 | 0.0001 | 0.001 | 0.0 | 0.0 |
| Compound 28 | 0.0 | 0.0 | 0.0001 | 0.001 | 0.0 | 0.0 | 0.0001 | 0.001 |
| Purified Water USP | Q.S | Q.S | Q.S | Q.S | Q.S | Q.S | Q.S | Q.S |

The coating solution can be prepared by mixing the designated amount of ingredients with continuous stirring. The resulting suspension can then be used according to coating procedure established for the specific tablet. The coating can be used to coat a variety of tablets, including compressed tablets, to an acceptable weight gain. The tablet can provide a cooling sensation in the mouth and/or throat upon oral administration. In one example, this coating can be applied to MSR cold/flu medications. In another example, this coating can be applied to medications intended for treatment of heartburn. In another example, this coating can be applied to medications intended for the treatment of allergies.

Example 8

Topical Ointment

TABLE 11

Soothing Topical Ointment

| | 8A | 8B | 8C | 8D | 8E | 8F |
|---|---|---|---|---|---|---|
| Petrolatum | Q.S. | Q.S. | Q.S. | — | — | 10 |
| Water | — | — | — | Q.S. | Q.S. | Q.S. |
| Ethanol | — | — | — | — | — | 20 |
| Eucalyptol | 6.655 | 0.7 | 1.305 | 0.25 | 0.45 | 5.00 |
| α-pinene | 2.5 | 0.5 | 0.3 | 0.05 | 0.1 | 1.3 |
| β-pinene | 0.3 | 0.01 | 0.3 | 0.05 | 0.05 | 1.5 |
| α-phellandrene | — | — | 0.01 | 0.01 | 0.01 | 0.5 |
| Limonene | 0.003 | 0.0006 | 0.0003 | 0.01 | — | 0.008 |
| Linalool | 0.0001 | 0.0001 | 0.0003 | — | 0.0005 | 0.001 |
| Benzyl Alcohol | — | — | — | — | 0.0001 | — |
| Geraniol | — | — | — | — | 0.0002 | 0.001 |
| Chamomile Oil | 0.0001 | — | 0.15 | 0.10 | — | — |
| Sodium Laureth-3-Sulfate | — | — | — | 11.80 | 11.80 | — |
| Cocamido-propyl Betaine | — | — | — | 3.25 | 3.25 | — |
| Sodium Lauroyl Sarcosinate | — | — | — | 0.50 | 0.50 | — |
| Poly-quaternium-10 | — | — | — | 0.10 | 0.10 | — |
| PEG-200 Glyceryl Palmate | — | — | — | 1.00 | 1.00 | — |
| Potassium Sorbate | — | — | — | 0.25 | 0.25 | — |

TABLE 11-continued

Soothing Topical Ointment

| | 8A | 8B | 8C | 8D | 8E | 8F |
|---|---|---|---|---|---|---|
| Sodium Benzoate | — | — | — | 0.25 | 0.25 | 0.1 |
| Citric Acid Anhydrous | — | — | — | 0.30 | 0.30 | — |
| Sodium Citrate | — | — | — | 1.00 | 1.00 | — |
| Compound 28 - Fraction 1 | 0.05 | 0.005 | — | 0.001 | 0.01 | — |
| Compound 28 - Fraction 2 | — | 0.005 | — | 0.001 | — | — |
| Compound 776 | — | — | 0.05 | — | — | 0.01 |

TABLE 12

Topical Ointment

| | 8G | 8H | 8I | 8J | 8K |
|---|---|---|---|---|---|
| Camphor (synthetic) | 4.8 | 4.8 | 4.8 | 4.8 | 4.8 |
| Eucalyptus oil | 1.2 | 1.2 | 1.2 | 1.2 | 1.2 |
| Menthol | 2.6 | 2.6 | 2.6 | 2.6 | 2.6 |
| Cedarleaf Oil | 0.44 | 0.44 | 0.44 | 0.44 | 0.44 |
| Nutmeg Oil | 0.54 | 0.54 | 0.54 | 0.54 | 0.54 |
| Thymol | 0.09 | 0.09 | 0.09 | 0.09 | 0.09 |
| Turpentine Oil | 2.00 | 2.00 | 2.00 | 2.00 | 2.00 |
| Petrolatum | Q.S. | Q.S. | Q.S. | Q.S. | Q.S. |
| Compound 28 - Fraction 1 | 0.02% | 0.01% | — | 0.005% | — |
| Compound 28 - Fraction 2 | — | 0.01% | — | — | — |
| Compound 776 | — | — | 0.02% | — | 0.001% |

Examples 8A-8K can be made using techniques known to those skilled in the art, which can include combining the ingredients in the specified amount and mixing until the composition is uniform. The compositions in Example 8 can be applied to the chest and throat and can temporarily relieve cough due to throat and/or bronchial irritation associated with a cold and/or flu. The compositions in Example 8 can also be applied to muscles and join to relieve minor aches and pains of muscles and joints.

Example 9

Vapor Inhaler

TABLE 13

Vapo Inhaler Composition

| | 9A | 9B | 9C | 9D | 9E | 9F |
|---|---|---|---|---|---|---|
| Levmetamfetamine | 20.8 | 24.0 | 33.0 | — | — | — |
| Levomenthol | 40.0 | 35.0 | 30.0 | 50.6 | 46.1 | 44.7 |
| Camphor | 30.0 | 35.0 | 28.0 | 37.9 | 46.0 | 41.7 |
| Lavender Oil | 2.0 | — | 3.0 | 2.5 | — | 4.5 |
| Methyl Salicylate | 7.0 | 6.0 | 6.0 | 8.8 | 7.9 | 8.9 |
| Bornyl Acetate | 0.1 | — | 0.1 | 0.12 | — | 0.15 |
| Compound 28 - Fraction 1 | 0.0001 | 0.00005 | — | 0.0001 | 0.00005 | — |
| Compound 28 - Fraction 2 | — | 0.00005 | — | — | 0.00005 | — |
| Compound 776 | — | — | 0.0001 | — | — | 0.0001 |

The ingredients of Examples 9A-9F can be mixed together in a stainless steel tank until dissolved and uniform. The formulation can then be absorbed onto a cellulose wick, which is enclosed inside the inhaler body. The inhaler body can be a rigid, injection-molded nosepiece and cover. When inhaled, the compositions of Example 9 can provide relief of nasal congestion due to the common cold and/or hay fever or upper respiratory allergies.

Example 10

Nasal Spray

TABLE 14

Nasal Spray

| | 10A | 10B | 10C | 10D | 10E | 10F | 10G | 10H |
|---|---|---|---|---|---|---|---|---|
| Oxymetazoline HCl | 0.0488 | 0.0494 | 0.0488 | 0.0494 | 0.0488 | 0.0494 | 0.0488 | 0.0494 |
| Benzalkonium Chloride | 0.04 | 0.04 | 0.04 | 0.04 | 0.04 | 0.04 | 0.04 | 0.04 |
| Benzyl Alcohol | 0.2 | 0.2 | 0.2 | 0.2 | 0.2 | 0.2 | 0.2 | 0.2 |
| Disodium EDTA | 0.01 | 0.01 | 0.01 | 0.01 | 0.01 | 0.01 | 0.01 | 0.01 |
| Sodium Citrate Dihydrate | 0.85 | 0.85 | 0.85 | 0.85 | 0.85 | 0.85 | 0.85 | 0.85 |
| Citric Acid Anhydrous | 0.2 | 0.2 | 0.2 | 0.2 | 0.2 | 0.2 | 0.2 | 0.2 |
| Polysorbate 80 | 0.5 | 0.2 | 0.5 | 0.2 | 0.5 | 0.2 | 0.5 | 0.2 |
| Sorbitol | 5 | — | 7 | — | 5 | — | 7 | — |
| Compound 776 | 0.0001 | 0.001 | 0.0 | 0.0 | 0.000001 | 0.00001 | — | — |
| Comound 28 | 0.0 | 0.0 | 0.0001 | 0.001 | 0.0 | 0.0 | 0.000001 | 0.00001 |
| Water | Q.S | Q.S | Q.S | Q.S | Q.S. | Q.S. | Q.S. | Q.S. |

The ingredients of Examples 10A-10H can be mixed together until there is a uniform solution. The nasal spray can help relieve nasal congestion that can accompany colds, hay fever, or upper respiratory allergies. It can be an effective nasal decongestant that can help alleviate sinus pressure and can also help shrink swollen nasal membranes to help a user breather more freely. The liquid composition can be administered by a spray bottle. Two or three sprays can be administered to each nostril and inhaled. In one example, nasal sprays can be less irritating if they contain the coolants of the present invention as compared to nasal sprays without the coolants.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A medication composition providing a cool sensation wherein the composition comprises a compound comprising the following structure:

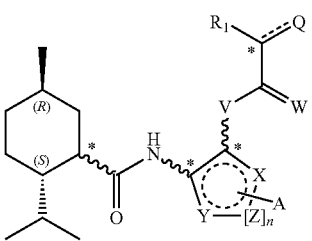

R$_1$ is selected from H, alkyl, amino alkyl, alkoxy;
Q=H$_2$, O, —OR$_1$, —N(R$_1$)$_2$, —OPO(OR$_1$)$_x$, —PO(OR$_1$)$_x$, —P(OR$_1$)$_x$ where x=1-2;
V=NR$_1$, O, —OPO(OR$_1$)$_x$, —PO(OR$_1$)$_x$, —P(OR$_1$)$_x$ where x=1-2;
W=H$_2$, O;
X, Y=independently selected from H, aryl, naphthyl for n=0;
X, Y=aliphatic CH$_2$ or aromatic CH for n≥1 and Z is selected from aliphatic CH$_2$, aromatic CH, or heteroatom;
A=lower alkoxy, lower alkylthio, aryl, substituted aryl or fused aryl; and
stereochemistry is variable at the positions marked*.

2. The composition of claim 1, wherein the compound activates at least one of TRPA1, TRPV1, or TRPM8.

3. The composition of claim 2, wherein the compound at a concentration of about 5.2E-5% provides:
   a) greater activation of TRPM8 than WS5 at a concentration of about 30 mM;
   b) greater activation of TRPA1 than allyl isothiocyanate at a concentration of about 50 mM; and
   c) greater activation of TRPV1 than capsaicin at a concentration of about 350 nM.

4. The composition of claim 2, wherein the compound at a concentration of about 5.2E-5% provides:
   a) at least about 110% activation of TRPM8 when compared to WS5 at a concentration of about 30 mM;
   b) at least about 180% activation of TRPA1 when compared to allyl isothiocyanate at a concentration of about 50 mM; and
   c) at least about 100% activation of TRPV1 when compared to capsaicin at a concentration of about 350 nM.

5. The composition of claim 2, wherein the compound at a concentration of about 5.2E-5% provides greater activation of TRPM8 than WS5 at a concentration of about 30 mM.

6. The composition of claim 1, wherein the structure comprises:

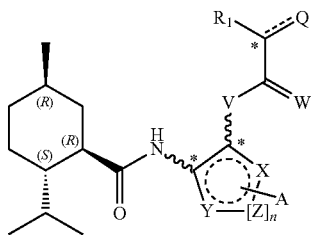

R$_1$ is selected from H, alkyl, amino alkyl, alkoxy;
Q=H$_2$, O, —OR$_1$, —N(R$_1$)$_2$, —OPO(OR$_1$)$_x$, —PO(OR$_1$)$_x$, —P(OR$_1$)$_x$ where x=1-2;
V=NR$_1$, O, —OPO(OR$_1$)$_x$, —PO(OR$_1$)$_x$, —P(OR$_1$)$_x$ where x=1-2;
W=H$_2$, O;
X, Y=independently selected from H, aryl, naphthyl for n=0;
X, Y=aliphatic CH$_2$ or aromatic CH for n≥1 and Z is selected from aliphatic CH$_2$, aromatic CH, or heteroatom;
A=lower alkoxy, lower alkylthio, aryl, substituted aryl or fused aryl; and
stereochemistry is variable at the positions marked*.

7. The composition of claim 6, wherein the structure comprises:

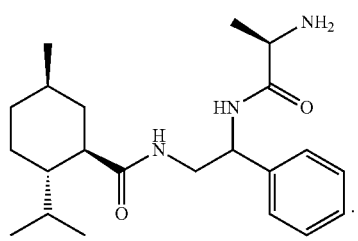 [SMILES: CC(C)[C@@H]1CC[C@@H](C)C[C@H]1C(=O)NCC(NC(=O)[C@@H](C)N)c1ccccc1]

8. The composition of claim 1, where the structure comprises:

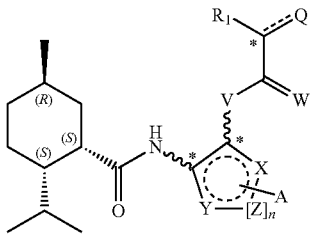

R$_1$ is selected from H, alkyl, amino alkyl, alkoxy;
Q=H$_2$, O, —OR$_1$, —N(R$_1$)$_2$, —OPO(OR$_1$)$_x$, —PO(OR$_1$)$_x$, —P(OR$_1$)$_x$ where x=1-2;
V=NR$_1$, O, —OPO(OR$_1$)$_x$, —PO(OR$_1$)$_x$, —P(OR$_1$)$_x$ where x=1-2;
W=H$_2$, O;
X, Y=independently selected from H, aryl, naphthyl for n=0;
X, Y=aliphatic CH$_2$ or aromatic CH for n≥1 and Z is selected from aliphatic CH$_2$, aromatic CH, or heteroatom;
A=lower alkoxy, lower alkylthio, aryl, substituted aryl or fused aryl; and
stereochemistry is variable at the positions marked*.

9. The composition of claim 1 wherein the composition is a liquid composition.

10. The composition of claim 9 wherein the composition further comprises an active.

11. The composition of claim 10 wherein the active is selected from the group consisting of acetaminophen, ibuprofen, naproxen, dextromethorphan, phenylephrine, pseudophedrine, guaifenesin, doxylamine succinate, and combinations thereof.

12. The composition of claim 9 wherein the composition does not comprise a drug active.

* * * * *

SEQUENCE LISTING

<160> NUMBER OF SEQ ID NOS: 3

<210> SEQ ID NO 1
<211> LENGTH: 2520
<212> TYPE: DNA
<213> ORGANISM: Homo sapiens

<400> SEQUENCE: 1

| | | | | | | |
|---|---|---|---|---|---|---|
| atgaagaaat | ggagcagcac | agacttgggg | gcagctgcgg | acccactcca | aaaggacacc | 60 |
| tgcccagacc | ccctggatgg | agaccctaac | tccaggccac | ctccagccaa | gccccagctc | 120 |
| tccacggcca | agagccgcac | ccggctcttt | gggaagggtg | actcggagga | ggctttcccg | 180 |
| gtggattgcc | ctcacgagga | aggtgagctg | gactcctgcc | cgaccatcac | agtcagccct | 240 |
| gttatcacca | tccagaggcc | aggagacggc | cccaccggtg | ccaggctgct | gtcccaggac | 300 |
| tctgtcgccg | ccagcaccga | gaagacccte | aggctctatg | atcgcaggag | tatctttgaa | 360 |
| gccgttgctc | agaataactg | ccaggatctg | agagcctgc | tgctcttcct | gcagaagagc | 420 |
| aagaagcacc | tcacagacaa | cgagttcaaa | gaccctgaga | cagggaagac | ctgtctgctg | 480 |
| aaagccatgc | tcaacctgca | cgacggacag | aacaccacca | tcccctgct | cctggagatc | 540 |
| gcgcggcaaa | cggacagcct | gaaggagctt | gtcaacgcca | gctacacgga | cagctactac | 600 |
| aagggccaga | cagcactgca | catcgccatc | gagagacgca | acatggccct | ggtgaccctc | 660 |
| ctggtggaga | acggagcaga | cgtccaggct | gcggcccatg | gggacttctt | taagaaaacc | 720 |
| aaagggcggc | tggattcta | cttcggtgaa | ctgccctgt | ccctggccgc | gtgcaccaac | 780 |
| cagctgggca | tcgtgaagtt | cctgctgcag | aactcctggc | agacggccga | catcagcgcc | 840 |
| agggactcgg | tgggcaacac | ggtgctgcac | gccctggtgg | aggtggccga | caacacggcc | 900 |
| gacaacacga | agtttgtgac | gagcatgtac | aatgagattc | tgatcctggg | ggccaaactg | 960 |
| cacccgacgc | tgaagctgga | ggagctcacc | aacaagaagg | gaatgatgcc | gctggctctg | 1020 |
| gcagctggga | ccgggaagat | cggggtcttg | gcctatattc | tccagcggga | gatccaggag | 1080 |
| cccgagtgca | ggcacctgtc | caggaagttc | accgagtggg | cctacgggcc | cgtgcactcc | 1140 |
| tcgctgtacg | acctgtcctg | catcgacacc | tgcgagaaga | actcggtgct | ggaggtgatc | 1200 |
| gcctacagca | gcagcgagac | ccctaatcgc | cacgacatgc | tcttggtgga | gccgctgaac | 1260 |
| cgactcctgc | aggacaagtg | ggacagattc | gtcaagcgca | tcttctactt | caacttcctg | 1320 |
| gtctactgcc | tgtacatgat | catcttcacc | atggctgcct | actacaggcc | cgtggatggc | 1380 |
| ttgcctccct | ttaagatgga | aaaaactgga | gactatttcc | gagttactgg | agagatcctg | 1440 |
| tctgtgttag | gaggagtcta | cttcttttc | cgagggattc | agtatttcct | gcagaggcgg | 1500 |
| ccgtcgatga | agaccctgtt | tgtggacagc | tacagtgaga | tgcttttctt | tctgcagtca | 1560 |
| ctgttcatgc | tggccaccgt | ggtgctgtac | ttcagccacc | tcaaggagta | tgtggcttcc | 1620 |
| atggtattct | ccctggcctt | gggctggacc | aacatgctct | actacacccg | cggtttccag | 1680 |
| cagatgggca | tctatgccgt | catgatagag | aagatgatcc | tgagagacct | gtgccgtttc | 1740 |
| atgtttgtct | acatcgtctt | cttgttcggg | ttttccacag | cggtggtgac | gctgattgaa | 1800 |
| gacgggaaga | tgactcccct | gccgtctgag | tccacgtcgc | acaggtggcg | ggggcctgcc | 1860 |
| tgcaggcccc | ccgatagctc | ctacaacagc | ctgtactcca | cctgcctgga | gctgttcaag | 1920 |
| ttcaccatcg | gcatgggcga | cctggagttc | actgagaact | atgacttcaa | ggctgtcttc | 1980 |
| atcatcctgc | tgctggccta | tgtaattctc | acctacatcc | tcctgctcaa | catgctcatc | 2040 |
| gccctcatgg | gtgagactgt | caacaagatc | gcacaggaga | gcaagaacat | ctggaagctg | 2100 |

| | |
|---|---:|
| cagagagcca tcaccatcct ggacacggag aagagcttcc ttaagtgcat gaggaaggcc | 2160 |
| ttccgctcag gcaagctgct gcaggtgggg tacacacctg atggcaagga cgactaccgg | 2220 |
| tggtgcttca gggtggacga ggtgaactgg accacctgga acaccaacgt gggcatcatc | 2280 |
| aacgaagacc cgggcaactg tgagggcgtc aagcgcaccc tgagcttctc cctgcggtca | 2340 |
| agcagagttt caggcagaca ctggaagaac tttgccctgg tccccctttt aagagaggca | 2400 |
| agtgctcgag ataggcagtc tgctcagccc gaggaagttt atctgcgaca gttttcaggg | 2460 |
| tctctgaagc cagaggacgc tgaggtcttc aagagtcctg ccgcttccgg ggagaagtga | 2520 |

<210> SEQ ID NO 2
<211> LENGTH: 3360
<212> TYPE: DNA
<213> ORGANISM: Homo sapiens

<400> SEQUENCE: 2

| | |
|---|---:|
| atgaagtgca gcctgaggaa gatgtggcgc cctggagaaa agaaggagcc ccagggcgtt | 60 |
| gtctatgagg atgtgccgga cgacacggag gatttcaagg aatcgcttaa ggtggttttt | 120 |
| gaaggaagtg catatggatt acaaaacttt aataagcaaa agaaattaaa acatgtgac | 180 |
| gatatggaca ccttcttctt gcattatgct gcagcagaag gccaaattga gctaatggag | 240 |
| aagatcacca gagattcctc tttggaagtg ctgcatgaaa tggatgatta tggaaatacc | 300 |
| cctctgcatt gtgctgtaga aaaaaccaa attgaaagcg ttaagtttct tctcagcaga | 360 |
| ggagcaaacc caaacctccg aaacttcaac atgatggctc ctctccacat agctgtgcag | 420 |
| ggcatgaata atgaggtgat gaaggtcttg cttgagcata gaactattga tgttaatttg | 480 |
| gaaggagaaa atgaaacac agctgtgatc attgcgtgca ccacaaataa tagcgaagca | 540 |
| ttgcagattt tgcttaacaa aggagctaag ccatgtaaat caaataaatg gggatgtttc | 600 |
| cctattcacc aagctgcatt ttcaggttcc aaagaatgca tggaaataat actaaggttt | 660 |
| ggtgaagagc atgggtacag tagacagttg cacattaact ttatgaataa tgggaaagcc | 720 |
| accccctctcc acctggctgt gcaaaatggt gacttggaaa tgatcaaaat gtgcctggac | 780 |
| aatggtgcac aaatagaccc agtggagaag ggaaggtgca cagccattca tttttgctgcc | 840 |
| acccagggag ccactgagat tgttaaactg atgatatcgt cctattctgg tagcgtggat | 900 |
| attgttaaca caaccgatgg atgtcatgag accatgcttc acagagcttc attgtttgat | 960 |
| caccatgagc tagcagacta tttaatttca gtgggagcag atattaataa gatcgattct | 1020 |
| gaaggacgct ctccacttat attagcaact gcttctgcat cttggaatat tgtaaatttg | 1080 |
| ctactctcta aggtgcccaa gtagacata aaagataatt ttggacgtaa ttttctgcat | 1140 |
| ttaactgtac agcaacctta tggattaaaaa atctgcgac ctgaatttat gcagatgcaa | 1200 |
| cagatcaaag agctggtaat ggatgaagac aacgatgggt gtactcctct acattatgca | 1260 |
| tgtagacagg gggccctgg ttctgtaaat aacctacttg gctttaatgt gtccattcat | 1320 |
| tccaaaagca agataagaa atcacctctg cattttgcag ccagttatgg gcgtatcaat | 1380 |
| acctgtcaga ggctcctaca agacataagt gatacgaggc ttctgaatga aggtgaccttt | 1440 |
| catggaatga ctcctctcca tctggcagca agaatggaca tgataaagt agttcagctt | 1500 |
| cttctgaaaa aggtgcatt gttttctcagt gaccacaatg gctggacagc tttgcatcat | 1560 |
| gcgtccatgg gcgggtacac tcagaccatg aaggtcattc ttgatactaa tttgaagtgc | 1620 |
| acagatcgct tggatgaaga cgggaacact gcacttcact ttgctgcaag ggaaggccac | 1680 |

| | |
|---|---|
| gccaaagccg ttgcgcttct tctgagccac aatgctgaca tagtcctgaa caagcagcag | 1740 |
| gcctcctttt tgcaccttgc acttcacaat aagaggaagg aggttgttct tacgatcatc | 1800 |
| aggagcaaaa gatgggatga atgtcttaag attttcagtc ataattctcc aggcaataaa | 1860 |
| tgtccaatta cagaaatgat agaataccte cctgaatgca tgaaggtact tttagatttc | 1920 |
| tgcatgttgc attccacaga agacaagtcc tgccgagact attatatcga gtataatttc | 1980 |
| aaatatcttc aatgtccatt agaattcacc aaaaaaacac ctacacagga tgttatatat | 2040 |
| gaaccgctta cagccctcaa cgcaatggta caaaataacc gcatagagct tctcaatcat | 2100 |
| cctgtgtgta aagaatattt actcatgaaa tggttggctt atggatttag agctcatatg | 2160 |
| atgaatttag gatcttactg tcttggtctc atacctatga ccattctcgt tgtcaatata | 2220 |
| aaaccaggaa tggctttcaa ctcaactggc atcatcaatg aaactagtga tcattcagaa | 2280 |
| atactagata ccacgaattc atatctaata aaaacttgta tgattttagt gttttttatca | 2340 |
| agtatatttg ggtattgcaa agaagcgggg caaattttcc aacagaaaag gaattatttt | 2400 |
| atggatataa gcaatgttct tgaatggatt atctacacga cgggcatcat ttttgtgctg | 2460 |
| cccttgtttg ttgaaatacc agctcatctg cagtggcaat gtggagcaat tgctgtttac | 2520 |
| ttctattgga tgaatttctt attgtatctt caaagatttg aaaattgtgg aatttttatt | 2580 |
| gttatgttgg aggtaatttt gaaaactttg ttgaggtcta cagttgtatt tatcttcctt | 2640 |
| cttctggctt ttggactcag cttttacatc ctcctgaatt tacaggatcc cttcagctct | 2700 |
| ccattgcttt ctataatcca gaccttcagc atgatgctag gagatatcaa ttatcgagag | 2760 |
| tccttcctag aaccatatct gagaaatgaa ttggcacatc cagttctgtc ctttgcacaa | 2820 |
| cttgtttcct tcacaatatt tgtcccaatt gtcctcatga atttacttat tggtttggca | 2880 |
| gttggcgaca ttgctgaggt ccagaaacat gcatcattga agaggatagc tatgcaggtg | 2940 |
| gaacttcata ccagcttaga gaagaagctg ccactttggt ttctacgcaa agtggatcag | 3000 |
| aaatccacca tcgtgtatcc caacaaaccc agatctggtg ggatgttatt ccatatattc | 3060 |
| tgtttttttat tttgcactgg ggaaataaga caagaaatac caaatgctga taaatcttta | 3120 |
| gaaatggaaa tattaaagca gaaataccgg ctgaaggatc ttacttttct cctggaaaaa | 3180 |
| cagcatgagc tcattaaact gatcattcag aagatggaga tcatctctga gacagaggat | 3240 |
| gatgatagcc attgttcttt tcaagacagg tttaagaaag agcagatgga acaaaggaat | 3300 |
| agcagatgga atactgtgtt gagagcagtc aaggcaaaaa cacaccatct tgagccttag | 3360 |

<210> SEQ ID NO 3
<211> LENGTH: 3315
<212> TYPE: DNA
<213> ORGANISM: Homo sapiens

<400> SEQUENCE: 3

| | |
|---|---|
| atgtccttcg agggagccag gctcagcatg aggagccgca gaaatggtac tatgggcagc | 60 |
| acccggaccc tgtactccag tgtatctcgg agcacagacg tgtcctacag tgacagtgat | 120 |
| ttggtgaatt ttattcaggc aaattttaaa aaacgagaat gtgtcttctt taccagagac | 180 |
| tccaaggcca tggagaacat atgcaagtgt ggttatgccc agagccagca catcgaaggc | 240 |
| acccagatca accaaaatga aagtggaac tacaaaaaac ataccaagga gtttccaaca | 300 |
| gacgccttcg gggacattca gtttgagact ctggggaaga aaggcaagta cttacgcttg | 360 |
| tcctgtgaca ccgactctga aactctctac gaactgctga cccagcactg gcacctcaaa | 420 |
| acacccaacc tggtcatttc agtgacgggt ggagccaaaa actttgcttt gaagccacgc | 480 |

```
atgcgcaaga tcttcagcag gctgatttac atcgcacagt ctaaaggtgc gtggattctc    540
actggaggca ctcactacgg cctgatgaag tacataggcg aggtggtgag agacaacacc    600
atcagcagga actcagaaga gaacatcgtg ccattggca tcgcagcatg gggcatggtc    660
tccaacaggg acaccctcat caggagctgt gatgatgagg acattttttc agctcaatac    720
atcatggatg actttaccag agaccctcta tacatcctgg acaacaacca tacccacctg    780
ctgcttgtgg acaacggttg tcatggacac cccacagtgg aagccaagct ccggaatcag    840
ctggaaaagt acatctctga gcgcaccagt caagattcca actatggtgg taagatcccc    900
atcgtgtgtt tgcccaagg aggtggaaga gagactctaa aagccatcaa cacctctgtc    960
aaaagcaaga tcccttgtgt ggtggtggaa ggctcggggc agattgctga tgtgatcgcc   1020
agcctggtgg aggtggagga tgttttaacc tcttccatgg tcaaagagaa gctggtacgc   1080 ttttttaccac gcactgtgtc ccggctgcct gaagaggaaa ttgagagctg atcaaatgg   1140 ctcaaagaaa tcttgagag ttctcaccta ctcacagtaa ttaagatgga agaggctgga   1200
gatgagattg tgagcaacgc catttcctat gcgctgtaca agccttcag cactaatgag   1260 caagacaagg acaactggaa tggacagctg aagcttctgc tggagtggaa ccagttggac   1320
cttgccagtg atgagatctt caccaatgat cgccgctggg agtctgccga ccttcaggag   1380
gtcatgttca cggctctcat aaaggacaga cccaagtttg tccgcctctt tctgagaat   1440 ggcctgaatc tgcagaagtt tctcaccaat gaagtcctca cagagctctt ctccacccac   1500
ttcagcaccc tagtgtaccg gaatctgcag atcgccaaga actcctacaa tgacgcactc   1560
ctcacctttg tctggaagtt ggtggcaaac ttccgtcgaa gcttctggaa agaggacaga   1620
agcagcaggg aggacttgga tgtggaactc catgatgcat ctctcaccac ccggcacccg   1680
ctgcaagctc tcttcatctg gccattctt cagaacaaga aggaactctc caaggtcatt   1740
tgggagcaga ccaaaggctg tactctggca gccttggggg ccagcaagct tctgaagacc   1800
ctggccaaag ttaagaatga tatcaacgct gctggggaat cggaggaact ggccaatgaa   1860
tatgagaccc gagcagtgga gttgttcacc gagtgttaca gcaatgatga agacttggca   1920
gaacagctac tggtctactc ctgcgaagcc tggggtggga gcaactgtct ggagctggca   1980
gtggaggcta cagatcagca tttcatcgct cagcctgggg tccagaattt cctttctaag   2040
caatggtatg agagatttc ccgagacacg aagaactgga agattatcct gtgtctattc   2100
atcatcccct agtgggctg tggcctcgta tcatttagga agaaacccat gacaagcac   2160 aagaagctgc tgtggtacta tgtggccttc ttcacgtcgc ccttcgtggt cttctcctgg   2220
aacgtggtct tctacatcgc cttcctcctg ctgtttgcct atgtgctgct catggacttc   2280
cactcagtgc cacacacccc cgagctgatc ctctacgccc tggtcttcgt cctcttctgt   2340
gatgaagtga ggcagtggta catgaacgga gtgaattatt tcaccgacct atggaacgtt   2400
atggacaccc tgggactctt ctacttcata gcgggtattg tattccggct ccactcttct   2460
aataaaagct cgttgtactc tgggcgcgtc atttttctgtc tggattacat tatattcacg   2520
ctaaggctca tccacatttt caccgtcagc aggaacttgg gacccaagat tataatgctg   2580
cagcggatgc tgatcgacgt tttcttcttc ctgttcctct ttgctgtgtg gatggtggcc   2640
tttggcgtgg ccagacaggg gatcctaagg caaaatgaac agcgctggag atggatcttc   2700
cgctctgtca tctatgagcc ctacctggcc atgtttggcc aggttcccag tgacgtggat   2760
agtaccacat atgacttctc ccactgtacc ttctcgggaa atgagtccaa gccactgtgt   2820
```

```
gtggagctgg atgagcacaa cctgccccgc ttccctgagt ggatcaccat tccgctggtg    2880
tgcatctaca tgctctccac caatatcctt ctggtcaacc tcctggtcgc catgtttggc    2940
tacacggtag gcattgtaca ggagaacaac gaccaggtct ggaaattcca gcggtacttc    3000
ctggtgcagg agtactgcaa ccgcctaaac atccccttcc ccttcgttgt cttcgcttat    3060
ttctacatgg tggtgaagaa gtgtttcaaa tgctgctgta aagagaagaa tatggagtct    3120
aatgcctgct gtttcagaaa tgaggacaat gagactttgg cgtgggaggg tgtcatgaag    3180
gagaattacc ttgtcaagat caacacgaaa gccaacgaca actcagagga gatgaggcat    3240
cggtttagac aactggactc aaagcttaac gacctcaaaa gtcttctgaa agagattgct    3300
aataacatca agtaa                                                     3315
```